(12) United States Patent
Moon et al.

(10) Patent No.: US 10,647,723 B2
(45) Date of Patent: May 12, 2020

(54) THIOCHROMENE TYPE COMPOUND AND USE THEREOF

(71) Applicant: SOGANG UNIVERSITY RESEARCH FOUNDATION, Seoul (KR)

(72) Inventors: Bong-Jin Moon, Seoul (KR); Han-Bin Oh, Seoul (KR); Na-Na Kang, Seoul (KR); Ae-Ran Jeon, Seoul (KR); Kye-Shin Park, Seoul (KR); Je-Hyun Baek, Seoul (KR)

(73) Assignee: SOGANG UNIVERSITY RESEARCH FOUNDATION, Seoul (KR)

( * ) Notice: Subject to any disclaimer, the term of this patent is extended or adjusted under 35 U.S.C. 154(b) by 0 days.

(21) Appl. No.: 15/577,239

(22) PCT Filed: Jun. 18, 2015

(86) PCT No.: PCT/KR2015/006167
§ 371 (c)(1),
(2) Date: May 11, 2018

(87) PCT Pub. No.: WO2016/190475
PCT Pub. Date: Dec. 1, 2016

(65) Prior Publication Data
US 2019/0375758 A1 Dec. 12, 2019

(30) Foreign Application Priority Data

May 27, 2015 (KR) .................. 10-2015-0073537

(51) Int. Cl.
*C07D 495/04* (2006.01)
*G01N 33/68* (2006.01)

(52) U.S. Cl.
CPC ....... *C07D 495/04* (2013.01); *G01N 33/6851* (2013.01)

(58) Field of Classification Search
CPC .................. C07D 495/04; G01N 33/6851
USPC ......................................... 548/400
See application file for complete search history.

(56) References Cited

U.S. PATENT DOCUMENTS

| 7,148,069 B2 | 12/2006 | Miyano et al. |
| 2008/0248584 A1 | 10/2008 | Shchepinov et al. |
| 2011/0223613 A1 | 9/2011 | Gut |

FOREIGN PATENT DOCUMENTS

| JP | 2007514691 A | 6/2007 |
| KR | 20090029848 A | 3/2009 |
| KR | 101627841 B1 | 6/2016 |
| WO | 2005058867 A1 | 6/2005 |
| WO | 2016190475 A1 | 12/2016 |

OTHER PUBLICATIONS

Moon, Bong-Jin; International Preliminary Report on Patentability for serial No. PCT/KR2015/006167, filed Jun. 18, 2015, dated Dec. 7, 2017, 14 pgs (8 pages of English Translation).
Moon, Bong-Jin; International Search Report & Written Opinion for serial No. PCT/KR2015/006167, filed Jun. 18, 2015, dated Jul. 8, 2016, 18 pgs. (9 pages of English Translation).
Moon, Bong-Jin; Grant of Patent for serial No. 10-2015-0073537, filed May 27, 2015, dated Mar. 22, 2016, 3 pgs. (2 pages of English Translation).
Moon, Bong-Jin; Written Opinion for serial No. 10-2015-0073537, filed May 27, 2015, dated Feb. 16, 2016, 8 pgs. (4 pages of English Translation).

*Primary Examiner* — Kristin A Vajda
(74) *Attorney, Agent, or Firm* — Taylor English Duma LLP

(57) ABSTRACT

This invention relates to a photocleavable mass tag and the use thereof, and particularly to a thiochromene-type compound useful for MALDI-TOF (Matrix-Assisted Laser Desorption/Ionization Time-Of-Flight) mass spectrometry or matrix-less LDI-TOF (Laser Desorption/Ionization Time-Of-Flight) mass spectrometry and the use thereof.

9 Claims, 9 Drawing Sheets

THIOCHROMENE TYPE COMPOUND AND USE THEREOF

CROSS-REFERENCE TO RELATED APPLICATIONS

This application is a 371 of International Patent Application No. PCT/KR2015/006167, filed Jun. 18, 2015, entitled "Thiochromene Type Compound and Use Thereof", the teaching of which is specifically and entirely incorporated herein by reference.

BACKGROUND OF THE INVENTION

The present invention relates to a photocleavable mass tag and the use thereof, and more particularly to a photocleavable mass tag, which may be easily photocleaved by a predetermined laser wavelength to thus release a specific mass-tagged cation so as to be efficiently used for MALDI-TOF (Matrix-Assisted Laser Desorption/Ionization Time-Of-Flight) mass spectrometry and matrix-less LDI-TOF (Laser Desorption/Ionization Time-Of-Flight) mass spectrometry. Also, the present invention relates to a technique for increasing the sensitivity of mass spectrometry using a compound for efficiently forming ions through light irradiation as a mass tag for mass spectrometry.

MALDI-TOF mass spectrometry is a method of analyzing the mass of a sample based on a difference in time of flight depending on m/z of ions generated in a manner in which the sample is crystallized through the addition of a matrix for absorbing UV light and is then ionized through laser irradiation. Such mass spectrometry is useful in the analysis of biopolymers such as proteins, as well as synthetic polymers, additives, and the like, because the absolute mass of a polymer may be measured with high sensitivity in a short time. However, since laser energy irradiated for an ionization process is transferred to the sample via the crystallized matrix to thereby ionize the sample, appropriate selection of a matrix has a great influence on test results. Accordingly, in order to obtain more accurate test results by removing the matrix, matrix-less LDI-TOF mass spectrometry has been devised.

Ferrocene-based novel photocleavable mass tags for forming stable cations have been synthesized. In this regard, Korean Patent Application No. 10-2014-0050964 (entitled: Photocleavable Mass Tag and Use Thereof) discloses the use of ferrocene in which a carbocation at the alpha position of ferrocene is stable, and the structure thereof is shown in FIG. 1. This patent document is incorporated by reference herein because ionization may be efficiently performed through laser irradiation in the absence of a matrix through introduction of a mass-changing group and a reactive group. The mass spectrometry spectrum results of the equimolar mixture of various ferrocene photocleavable mass tags are shown in FIG. 2.

Although the ferrocene-based mass tags are advantageous because of easy synthesis and high photocleavage efficiency compared to trityl derivatives, the solubility thereof in water is low, as in trityl derivatives, resulting in very low conjugation yields upon conjugation thereof with biomaterials such as peptides, nucleic acids, glycans, and the like, having high hydrophilicity and water solubility. Furthermore, with the goal of increasing the yield of conjugation with a biomaterial, even when a mixture of an organic solvent and water is used, the proportion of the organic solvent has to be increased in order to dissolve the hydrophobic ferrocene or trityl tag. During the conjugation, the three-dimensional structure of a biomaterial such as a protein or antibody may be deformed, thus losing the specificity of the protein or antibody, which is undesirable. Hence, in order to solve such problems, there is a need for the development of mass tags having high solubility in water.

As conventionally known mass tags, various mass tags, formed by introducing substituents having different masses to triphenylmethyl or trityl groups for relatively efficient formation of cations under specific conditions, and combinatorial synthesis methods thereof are known (Shchepinov et al, Nucl. Acids Symp. Ser. 1999, 42, 107-108). Such methods are characterized in that, under mass spectrometry conditions in which the molecular weight of a predetermined molecule is measured using a difference in time of flight (TOF) after ionization through laser irradiation, an analytical sample may be ionized even without a matrix for aiding the ionization.

There are known documents pertaining to a method of calibrating a mass spectrometer in a similar manner using a trityl derivative (M. S. Shchepinov et al, U.S. Pat. No. 6,734,025 B2, May 2004), an analysis technique using an oligomer library tagged with the above tag (E. M. Southern et al, U.S. Pat. No. 6,780,981 B1, August 2004), a technique for increasing the mass spectrometry sensitivity of a biomaterial using the above tag (M. S. Shchepinov et al, US 2008/0248584 A1), a technique for imaging a biosample using a mass spectrometer and an antibody tagged with the above tag (I. G. Gut, US 2011/0223613), and the like. These documents using MALDI-TOF are incorporated by reference herein.

Accordingly, the present invention is intended to provide a compound, which enables the formation of stable carbocation after photocleavage, has high absorbance at a predetermined laser wavelength (i.e. 355 nm), has a molecular weight of 500 Dalton or less to thus exhibit high solubility in water, has high hydrophilicity due to the presence of a heteroatom in a molecular structure thereof, may be easily synthesized at high yield, and has a structure to which a plurality of mass-changing groups may be easily introduced.

According to the present invention, a 2-alkylsulfanyl-2H-thiochromene derivative may be utilized as a photocleavable mass tag able to release a cation having a specific mass by being easily photocleaved under conditions of MALDI-TOF MS (Matrix-Assisted Laser Desorption/Ionization Time-Of-Flight Mass Spectrometry) in which a laser at 355 nm is applied. Furthermore, the thiochromene derivative according to the present invention is capable of generating cations using only a laser even under matrix-less LDI-TOF MS conditions, unlike conventional MALDI-TOF MS. Accordingly, noise caused by the addition of a matrix may be completely removed, and a polymer such as an antibody may be detected with high sensitivity.

Therefore, the present invention provides a thiochromene-type compound, particularly a 2-alkylthio-2H-thiochromene derivative compound, which is useful as a photocleavable mass tag. The principle thereof is shown in FIG. 3. Specifically, the compound according to the present invention is composed of a UV-absorbing group for absorbing UV light, a reactive group able to react with a biomaterial, a linker that enables the UV-absorbing group and the reactive group to be connected or cleaved through light irradiation, and a mass-changing group that may be substituted through a change in mass.

An aspect of the present invention provides a compound represented by Formula I below:

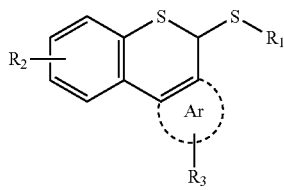

Formula I

In Formula I, R₁ is a linker having an active reactive group able to easily react with a functional group present on a solid or a biomaterial, such as an amine, thiol, or the like, examples of the active reactive group including a N-hydroxysuccinimide ester group, a N-hydroxysulfosuccinimide ester group, a pentafluorophenyl ester group, a 4-sulfo-2,3,5,6-tetrafluorophenyl ester group, a nitrophenyl ester group, a 2,4,5-trichlorophenyl ester group, a phthalimido ester group, a N-hydroxy-5-norbornen-endo-2,3-dicarboimide ester group, and a maleimide group. The connection portion of the linker may include, for example, an alkyl group, but is not limited thereto, and may be ether-containing alkyl, aryl or heteroaryl. Preferably, the connection portion of the linker is a C1-12 alkyl group, a C6-60 aryl group, or a C2-60 heteroaryl group having at least one heteroatom selected from among N, S and O.

As used herein, the term "alkyl group" refers to a C1-60 linear or branched alkyl group such as linear or branched alkyl, including a methyl group, an ethyl group, a propyl group, an isopropyl group, a N-butyl group, an isobutyl group, a tert-butyl group, a N-pentyl group, or a N-hexyl group, and preferably a C1-12 linear or branched alkyl group.

As used herein, the term "aryl group" refers to a C6-60 aryl group having a hydrocarbon ring, for example, a phenyl group, a naphthyl group, etc., and the term "heteroaryl group" refers to a C2-60 aromatic heteroaryl group containing at least one heteroatom selected from the group consisting of N, S and O at any possible position.

As used herein, the term "active reactive group" refers to a N-hydroxysuccinimide ester group, a N-hydroxysulfosuccinimide ester group, a pentafluorophenyl ester group, a 4-sulfo-2,3,5,6-tetrafluorophenyl ester group, a nitrophenyl ester group, a 2,4,5-trichlorophenyl ester group, a phthalimido ester group, a N-hydroxy-5-norbornen-endo-2,3-dicarboimide ester group, or a maleimide group. Preferably, the active reactive group is a N-hydroxysuccinimide ester group (NHS), a pentafluorophenyl ester group, a nitrophenyl ester group, or a maleimide group, and is more preferably a N-hydroxysuccinimide ester group.

In Formula I, R₂ and R₃ may be the same as each other, and are independently hydrogen, alkyl, aryl, alkoxy, alkylamino, alkylthio or a fused ring. Here, "alkyl" or "aryl" is as defined above.

As used herein, the term "alkoxy" refers to a linear or branched C1-12 alkoxy group, such as a methoxy group, an ethoxy group, a N-propoxy group, a N-butoxy group, an isobutoxy group, a tert-butoxy group, or a N-pentoxy group.

As used herein, the term "fused ring" refers to a ring obtained via the condensation of a phenyl group or an aromatic heterocyclic group containing at least one heteroatom selected from among O, S and N, at any possible position, with a benzene ring or an aromatic heterocyclic group containing 1 to 3 heteroatoms selected from among oxygen, sulfur and nitrogen atoms, and is any one selected from among, for example, pyrrole, thiophene, indole, furan, imidazole, triazole, diazole, and pyrimidine. Preferably, the fused ring is thiophene, pyrrole, indole, or furan.

In Formula I, Ar is a C6-60 aromatic ring, a heteroaromatic ring, or an extension ring achieved through a combination of heteroaromatic rings. The "heteroaromatic ring" may be a monocyclic or polycyclic hetero ring containing O, N or S as a heteroatom, the number of carbons of which is not particularly limited, but is preferably 2 to 60. Examples of the heterocyclic group may include, but are not limited to, a thiophene group, a furan group, a pyrrole group, an imidazole group, a thiazole group, an oxazole group, an oxadiazole group, a triazole group, a pyridyl group, a bipyridyl group, a triazine group, an acridyl group, a pyridazine group, a quinolinyl group, an isoquinoline group, an indole group, a benzoxazole group, a benzimidazole group, a benzothiazole group, a benzocarbazole group, a benzothiophene group, a dibenzothiophene group, a benzofuranyl group, a dibenzofuranyl group, and the like. Preferably, the heteroaromatic ring of Ar is benzene, pyrrole, thiophene, indole, furan, imidazole, triazole, diazole, or pyrimidine.

As used herein, the term "extension ring" refers to a fused ring compound of heteroaromatic rings.

When a hetero ring is introduced, the solubility of the tag in water may be increased, and the stability of the thiochromenylium cation that is produced may also be increased.

Another aspect of the present invention provides compounds of Formulas II to V below:

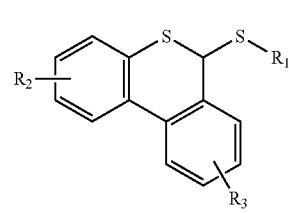

Formula II

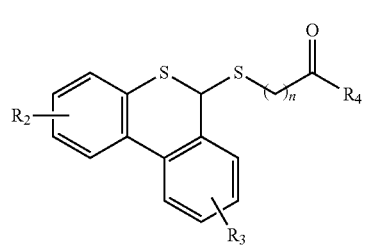

Formula III

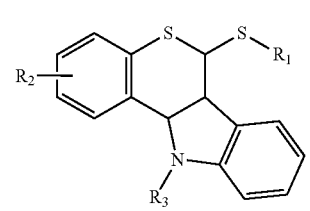

Formula IV

Formula V

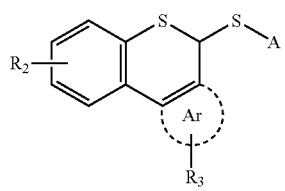

In Formulas II, III, IV and V, $R_1$, $R_2$ and $R_3$ are as defined in Formula I.

In Formulas III and V, $R_4$ and A are each a linker having an active reactive group able to easily react with any reactive group (amine, thiol, etc.) present on a solid or a biomaterial, preferable examples of the active reactive group including a N-hydroxysuccinimide ester group, a N-hydroxysulfosuccinimide ester group, a pentafluorophenyl ester group, a 4-sulfo-2,3,5,6-tetrafluorophenyl ester group, a nitrophenyl ester group, a 2,4,5-trichlorophenyl ester group, a phthalimido ester group, a N-hydroxy-5-norbornen-endo-2,3-dicarboimide ester group, and a maleimide group, and the connection portion of the linker is preferably a C1-12 alkyl group, a C6-60 aryl group, or a C2-60 heteroaryl group containing at least one heteroatom selected from among N, S and O.

In Formula III, n is an integer of 1-12.

Still another aspect of the present invention provides a photocleavable mass tag, and preferably a 2-alkylthio-2H-thiochromene derivative useful for MALDI-TOF or matrix-less MALDI-TOF. Such a derivative is represented by Formulas I to V.

The principle pertaining to the photocleavable mass tag according to the present invention is shown in FIG. 4. When a laser is applied at 355 nm, the alkylthio group at position 2 is subjected to heterolytic cleavage to thus easily form a thiochromenylium cation, which is then easily detected in a mass spectrometer. Thus, ionization may become easy through laser irradiation alone, thereby achieving high precision for MALDI-TOF mass spectrometry and matrix-less LDI-TOF mass spectrometry.

Preferable examples of the 2-alkylthio-2H-thiochromene-type mass tag according to the present invention are compounds 1, 2, and 3 (3a-3d) below.

1

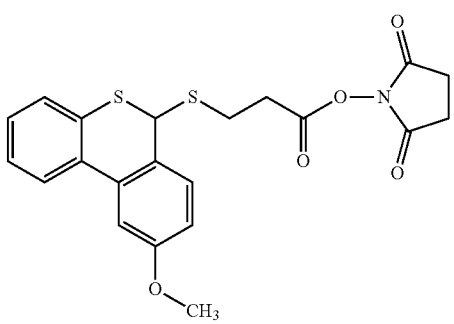

2

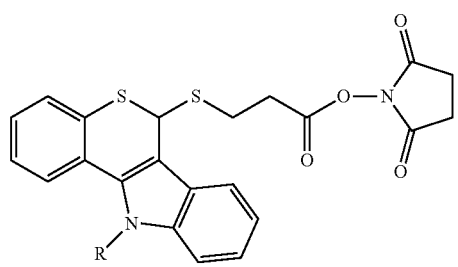

3a: R = Me
3b: R = Et
3c: R = n-Pr
3d: R = n-Bu

Compounds 1, 2 and 3 have a fundamental backbone of 2-alkylthio-2H-thiochromene and a NHS group (N-hydroxysuccinimidyl ester) able to react with an amine group at the terminal thereof.

For compound 2, an alkoxy group (MeO—) is introduced to benzene rings substituted at positions 3 and 4 of thiochromene. For compound 3, any functional group R may be introduced to N of the indole ring. The functional group R may be modified with Me, Et, n-Pr, n-Bu, or the like, or may be various modified in a manner similar thereto.

Yet another aspect of the present invention provides a method of synthesizing a photocleavable mass tag. For example, Synthesis Method 1 is exemplarily illustrated below. The synthesis of the mass tag according to the present invention is not limited to the following method.

Synthesis Method 1

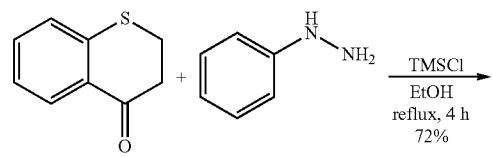

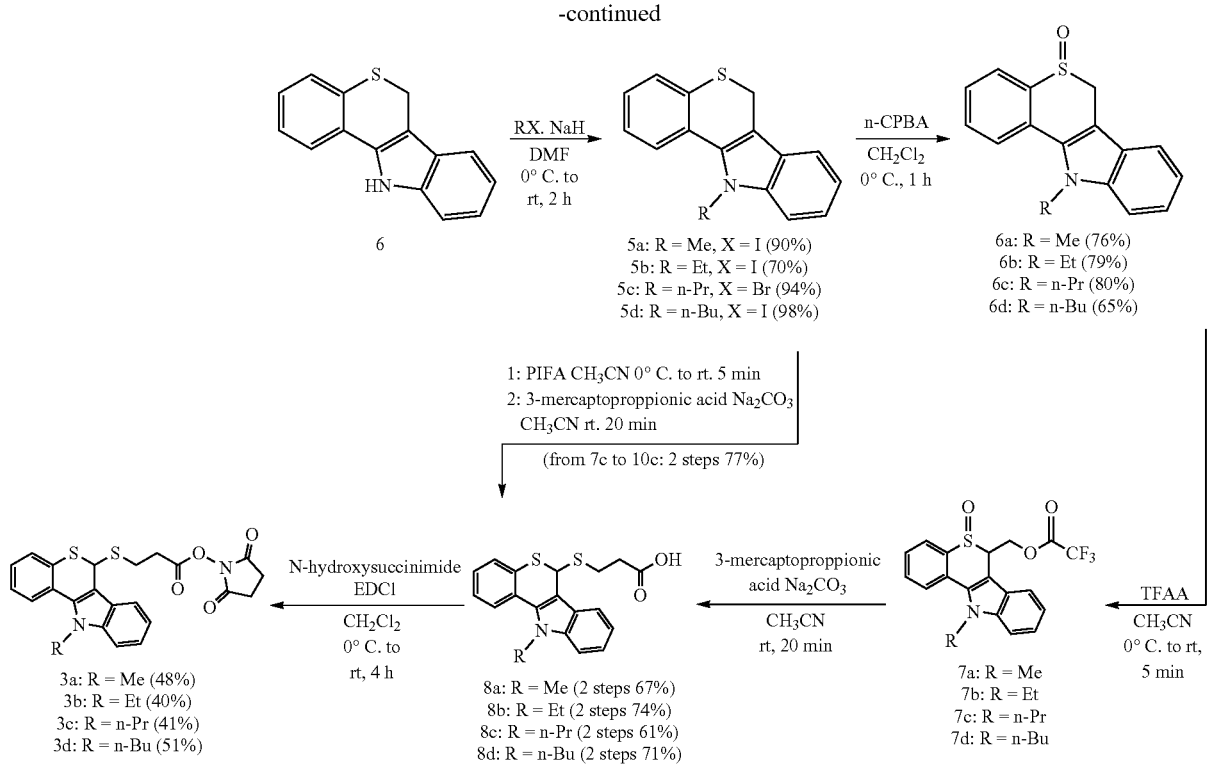

In accordance with Synthesis Method 1, thiochromeno[4,3-b]indole-based photocleavable mass tag derivatives (3a-3d) may be obtained with high efficiency. Also, in accordance with Synthesis Method 1, various thiochromene-type compounds may be synthesized at a high yield of about 15% using easily commercially available starting materials.

Preferably, the photocleavable mass tag according to the present invention is indole-introduced 2-alkylthio-2H-thiochromene of Formula 3a, 3b, 3c or 3d below.

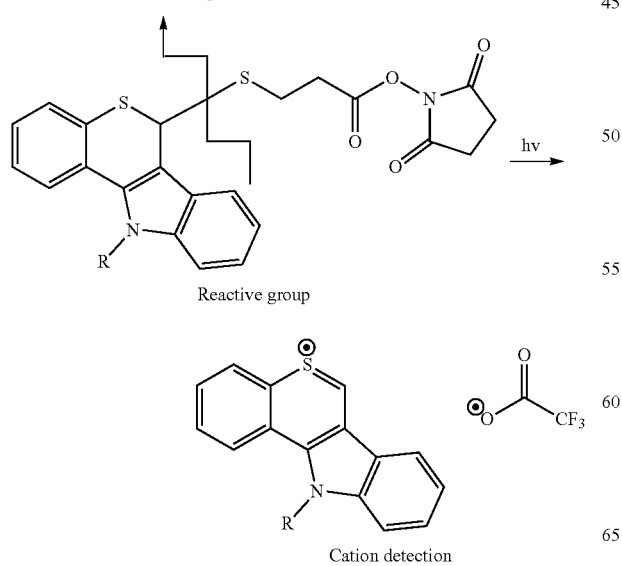

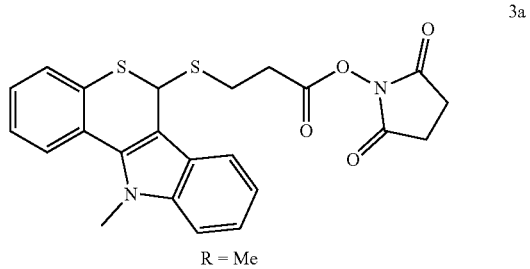

-continued

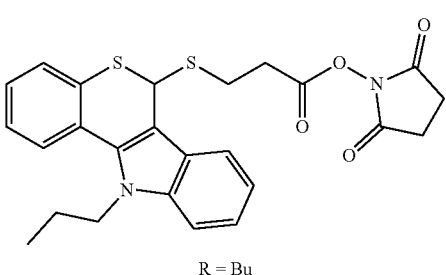

R = Bu

Still yet another aspect of the present invention provides a conjugate of a biomaterial and a mass tag represented by Formula Ia below.

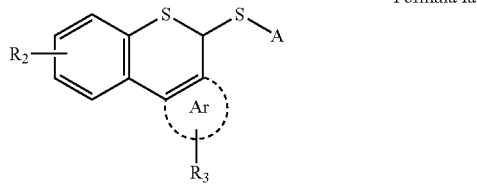

Formula Ia

In Formula Ia, A is a linker having an active reactive group able to easily react with any reactive group (amine, thiol, etc.) present on a solid or a biomaterial, examples of the active reactive group preferably including a N-hydroxysuccinimide ester group, a N-hydroxysulfosuccinimide ester group, a pentafluorophenyl ester group, a 4-sulfo-2,3,5,6-tetrafluorophenyl ester group, a nitrophenyl ester group, a 2,4,5-trichlorophenyl ester group, a phthalimido ester group, a N-hydroxy-5-norbornen-endo-2,3-dicarboimide ester group, and a maleimide group, and the connection portion of the linker is preferably a C1-12 alkyl group, a C6-60 aryl group, or a C2-60 heteroaryl group containing at least one heteroatom selected from among N, S and O.

Although not limited to the following, $R_2$ and $R_3$ are preferably hydrogen, a C1-12 alkyl, a C6-60 aryl, a C1-12 alkoxy, a C1-12 alkylamino, a C1-12 alkylthio, or a fused ring, and Ar may be an aromatic ring such as benzene, or a heteroaromatic ring selected from among pyrrole, thiophene, indole, imidazole, triazole, diazole and pyrimidine.

The biomaterial may be an antigen, an antibody, a biomarker, a peptide, a nucleic acid, a glycan, a cell tissue, etc., and may include a variety of polymer compounds regardless of the kinds thereof. For example, the molecular weight of a polymer compound is not limited, but may be 200,000 Da or more.

According to the present invention, a thiochromene-type compound can be easily synthesized and has high solubility in water. Also, the thiochromene-type compound according to the present invention, having peculiar photocleavability, can be utilized as a high-sensitivity mass tag not only for MALDI-TOF but also for matrix-less LDI-TOF. Particularly in matrix-less LDI-TOF, mass spectrometry results for various polymers can be obtained with high sensitivity due to the absence of a matrix.

BRIEF DESCRIPTION OF DRAWINGS

FIG. 5 shows the UV-Vis absorption spectrum results of compounds 1, 2 and 3a.

DETAILED DESCRIPTION OF THE INVENTION

Figure 1:
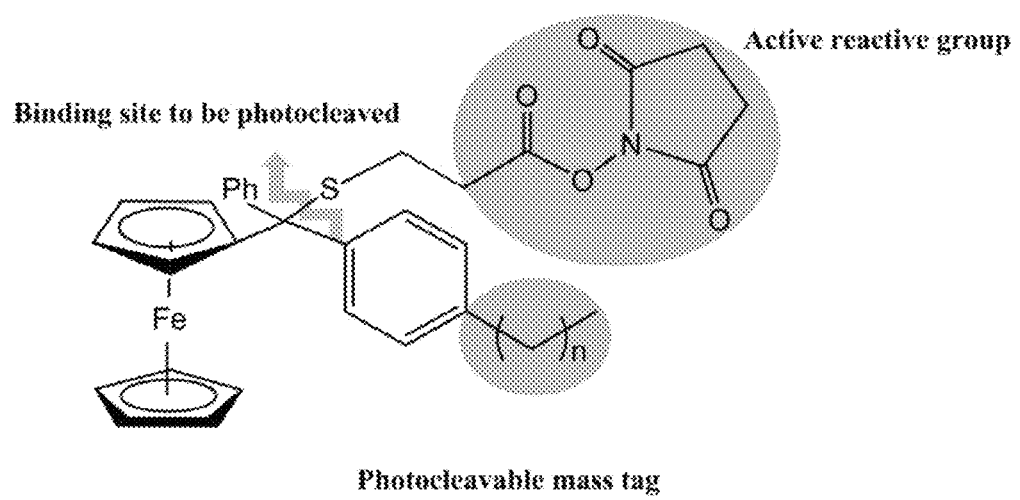
FIG. 1 shows a conventional ferrocene-based mass tag.
Figure 2:
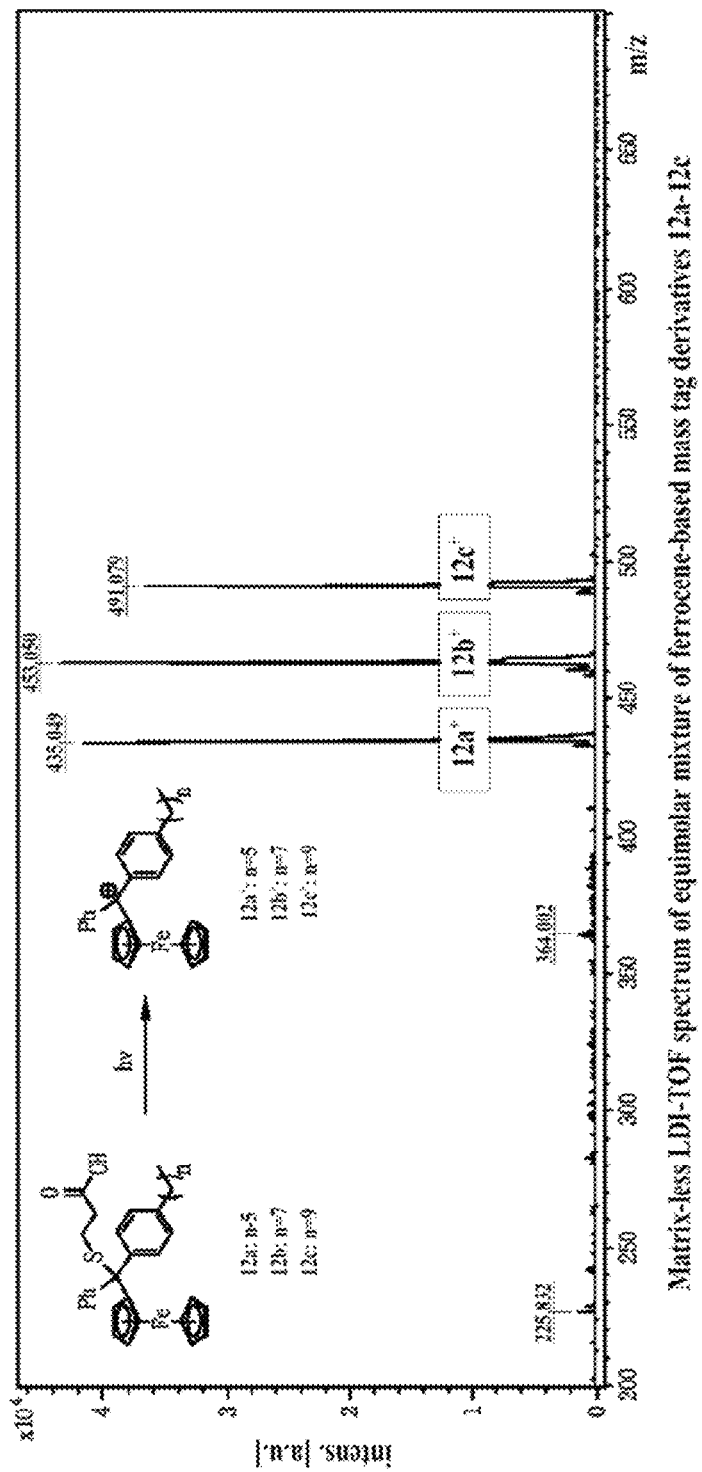
FIG. 2 shows the mass spectrometry spectrum results of ferrocene-based novel mass tags having different masses under matrix-less laser desorption/ionization conditions.
Figure 3:
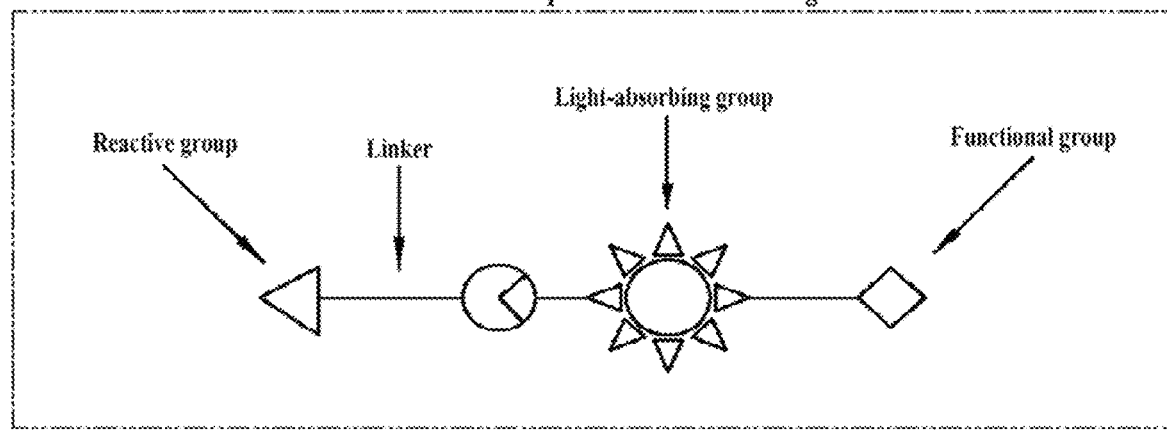
FIG. 3 shows the concept of a photocleavable mass tag.
Figure 4:
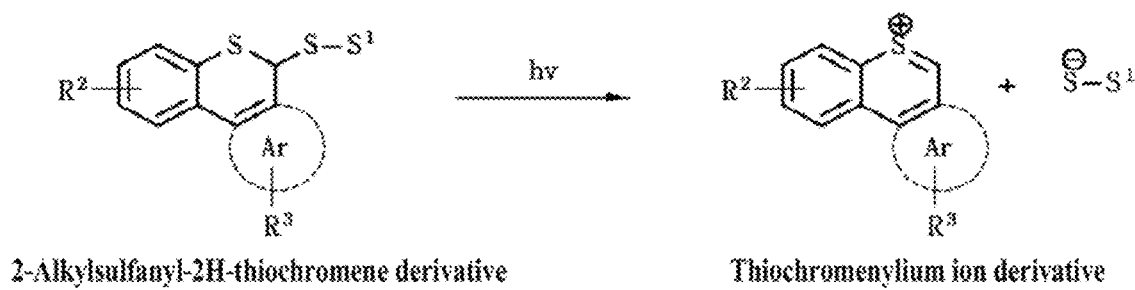
FIG. 4 shows the scheme of a 2-alkylthio-2H-thiochromene derivative-based photocleavable mass tag.

Example 1: Synthesis of Cleavable Mass Tag (I)

Mass tags 3a-3d were synthesized from thiochroman-4-one and phenyl hydrazine in accordance with the synthesis route in Synthesis Method 1.

(A) Synthesis of 6,11-dihydrothiochromeno[4,3-b]indole (4)

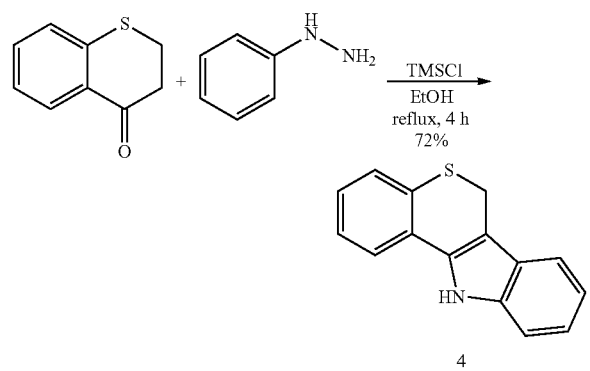

Thiochroman-4-one (11.4 g, 69.2 mmol) and phenyl hydrazine (7.49 g, 6.82 mL, 69.2 mmol) were dissolved in ethanol (100 mL) in a reactor, rapidly added with trimethylsilyl chloride (7.52 g, 8.79 mL, 69.2 mmol), and the reactor was then capped. The resulting reaction mixture was heated to reflux for 4 hr and then cooled. A saturated sodium bicarbonate aqueous solution was added until the solution became sufficiently basic, followed by dilution with ethyl acetate (150 mL). The organic layer was separated and the remaining water layer was extracted three times with ethyl acetate (250 mL×3). The combined organic layer was washed with a saturated sodium chloride aqueous solution, added with anhydrous sodium sulfate and filtered under reduced pressure. The filtered solvent was completely removed under reduced pressure, and the remaining solid was dispersed in diethyl ether and ethyl acetate at 8:1 (v/v) and then filtered, thus yielding compound 4 as a yellow liquid. (11.8 g, 49.7 mmol, 72%): mp=162-165° C.; $R_f$=0.33

(EtOAc:hexane=1:4); ¹H NMR (400 MHz, DMSO-d$_6$): δ 11.58 (s, 1H), 7.71 (d, J=7.2 Hz, 1H), 7.53 (d, J=8.0 Hz, 1H), 7.39 (d, J=8.0 Hz, 1H), 7.34 (d, J=7.6 Hz, 1H), 7.24 (dd, J=8.0, 7.2 Hz, 1H), 7.13-7.17 (m, 2H), 7.04 (dd, J=7.2, 7.0 Hz, 1H), 4.28 (s, 2H); ¹³C NMR (100 MHz, DMSO-d$_6$): δ 136.7, 132.4, 131.9, 127.5, 127.4, 127.2, 125.9, 125.8, 122.9, 122.4, 119.4, 118.5, 111.4, 105.9, 22.7; IR (ZnSe-ATR) 3336 (w), 1957 (w), 1915 (w), 1871 (w), 1785 (w), 1453 (w), 1440 (w), 1416 (w), 1312 (w), 1276 (w), 1177 (w), 1006 (w), 1036 (w), 918 (w), 864 (w), 761 (m), 733 (vs), 670 (w) cm⁻¹; Anal. Calcd for C$_{15}$H$_{11}$NS: C, 75.92; H, 4.67; N, 5.90; S, 13.51. Found: C, 75.92; H, 4.62; N, 5.91; S, 13.63.

(B) Synthesis of 11-alkyl-6,11-dihydrothiochromeno[4,3-b]indole (5a-5d)

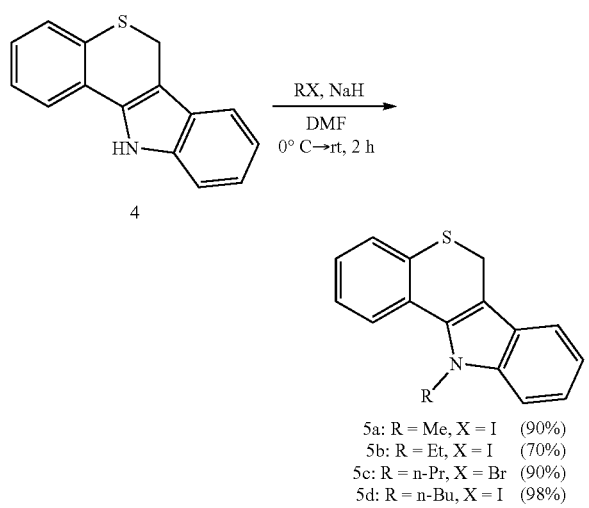

5a: R = Me, X = I (90%)
5b: R = Et, X = I (70%)
5c: R = n-Pr, X = Br (90%)
5d: R = n-Bu, X = I (98%)

In a nitrogen atmosphere, 6,11-dihydrothiochromeno[4,3-b]indole (4, 1.50 g, 6.32 mmol, 1.0 equiv) and sodium hydride (60%, dispersion in mineral oil, 0.556 g, 12.6 mmol, 2.0 equiv) were mixed together and anhydrous dimethylformamide (10 mL) was slowly added thereto at 0° C. The resulting reaction mixture was stirred at 0° C. for 30 min, rapidly added with alkyl halide (12.6 mmol, 2.0 equiv) in a nitrogen atmosphere, stirred at room temperature for 2 hr, and then sequentially added with water (10 mL) and ethyl acetate (30 mL). The organic layer was separated and the remaining water layer was extracted three times with ethyl acetate (40 mL×3). The combined organic layer was washed with a saturated sodium chloride aqueous solution, added with anhydrous sodium sulfate and filtered under reduced pressure. The solvent of the filtrate was completely removed under reduced pressure, followed by purification through column chromatography (hexane:ethyl acetate=15:1), thereby yielding compound 5 as a yellow liquid.

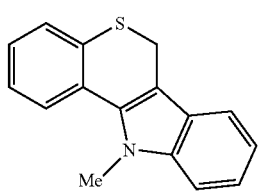

11-Methyl-6,11-dihydrothiochromeno[4,3-b]indole (5a): 90%; mp=94-97 C; R$_f$=0.32 (EtOAc:hexane=1:15); ¹HNMR (400 MHz, DMSO-d$_6$): δ 7.83 (d, J=7.6 Hz, 1H), 7.62 (d, J=8.0 Hz, 1H), 7.50-7.54 (m, 2H), 7.33 (dd, J=7.6, 6.8 Hz, 1H), 7.21-7.25 (m, 2H), 7.11 (d, J=7.6, 7.2 Hz, 1H), 4.15 (s, 2H), 3.95 (s, 3H); ¹³C NMR (100 MHz, DMSO-d$_6$): δ 138.5, 134.5, 133.7, 128.6, 127.8, 127.1, 126.2, 125.0, 124.1, 122.5, 119.8, 118.7, 110.3, 109.7, 32.8, 22.8; IR (ZnSe-ATR) 2887 (w), 1908 (w), 1875 (w), 1834 (w), 1470 (w), 1426 (w), 1360 (w), 1275 (w), 1235 (w), 1219 (w), 1121 (w), 1164 (w), 1082 (w), 1046 (w), 943 (w), 821 (w), 737 (vs), 714 (m), 675 (w) cm⁻¹; Anal. Calcd for C$_{16}$H$_{13}$NS: C, 76.46; H, 5.21; N, 5.57; S, 12.76. Found: C, 76.49; H, 5.22; N, 5.43; S, 12.64.

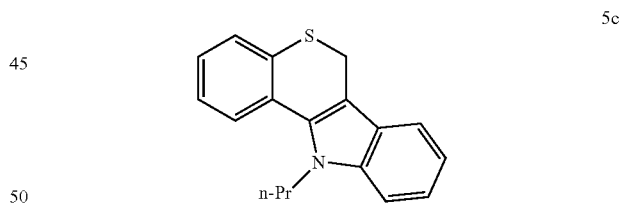

11-Ethyl-6,11-dihydrothiochromeno[4,3-b]indole (5b): 70%; mp=122-126 C; R$_f$=0.36 (EtOAc:hexane=1:15); ¹H NMR (400 MHz, DMSO-d$_6$): δ 7.68 (d, J=7.6 Hz, 1H), 7.63 (d, J=8.4 Hz, 1H), 7.51-7.56 (m, 2H), 7.35 (dd, J=7.6, 7.2 Hz, 1H), 7.21-7.26 (m, 2H), 7.12 (dd, J=7.6, 7.2 Hz, 1H), 4.40 (q, J=7.0 Hz, 2H), 4.13 (s, 2H), 1.39 (t, J=7.0 Hz, 3H); ¹³C NMR (100 MHz, DMSO-d$_6$): δ 137.7, 133.9, 133.7, 128.7, 127.7, 127.0, 126.4, 124.4, 124.3, 122.6, 119.8, 118.8, 118.7, 110.2, 22.7, 15.5, 15.4; IR (ZnSe-ATR) 2970 (w), 1936 (w), 1847 (w), 1477 (w), 1457 (w), 1363 (w), 1340 (w), 1284 (w), 1208 (w), 1162 (w), 1131 (w), 1086 (w), 1040 (w), 1102 (w), 784 (w), 746 (vs), 712 (w), 670 (w) cm⁻¹; Anal. Calcd for C$_{17}$H$_{15}$NS: C, 76.94; H, 5.70; N, 5.28; S, 12.08. Found: C, 76.88; H, 5.71; N, 5.29; S, 12.07.

11-Propyl-6,11-dihydrothiochromeno[4,3-b]indole (5c): 94%; mp=75-80° ° C.; R$_f$=0.40 (EtOAc:hexane=1:15); ¹H NMR (400 MHz, DMSO-d$_6$): δ 7.69 (d, J=8.0 Hz, 1H), 7.62 (d, J=7.6 Hz, 1H), 7.56 (d, J=8.4 Hz, 1H), 7.51 (d, J=7.6 Hz, 1H), 7.35 (dd, J=7.6, 7.2 Hz, 1H), 7.20-7.25 (m, 2H), 7.11 (dd, J=8.0, 7.2 Hz, 1H), 4.34 (t, J=7.2 Hz, 2H), 4.13 (s, 2H), 1.73 (tq, J=7.2, 7.2 Hz, 2H), 0.82 (t, J=7.2 Hz, 3H); ¹³C NMR (100 MHz, DMSO-d$_6$): δ 138.2, 133.9, 133.8, 128.8, 128.0, 127.1, 126.4, 124.32, 124.26, 122.6, 119.8, 118.8, 110.6, 110.4, 46.1, 23.3, 22.7, 11.0; IR (ZnSe-ATR) 3056 (w), 2970 (w), 1475 (w), 1460 (w), 1414 (w), 1348 (w), 1204 (w), 1158 (w), 1039 (w), 1012 (w), 754 (m), 738 (vs), 669 (w) cm⁻¹; Anal. Calcd for C$_{18}$H$_{17}$NS: C, 77.38; H, 6.13; N, 5.01; S, 11.47. Found: C, 77.38; H, 6.17; N, 4.95; S, 11.35.

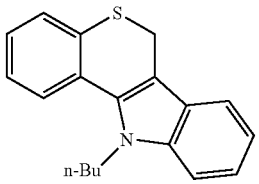

5d

11-Butyl-6,11-dihydrothiochromeno[4,3-b]indole (5d): 98%; mp=86-90 C; $R_f$=0.47 (EtOAc:hexane=1:15); $^1$H NMR (400 MHz, DMSO-d$_6$): δ 7.71 (d, J=7.6 Hz, 1H), 7.62 (d, J=8.0 Hz, 1H), 7.55 (d, J=8.4 Hz, 2H), 7.52 (d, J=8.0 Hz, 1H), 7.34 (dd, J=7.6, 7.2 Hz, 1H), 7.20-7.25 (m, 2H), 7.11 (dd, J=7.6, 7.2 Hz, 1H), 4.38 (t, J=7.6 Hz, 2H), 4.12 (s, 2H), 1.68 (tt, J=7.6, 7.6 Hz, 2H), 1.25 (tq, J=7.6, 7.2 Hz, 2H), 0.85 (t, J=7.2 Hz, 3H); $^{13}$C NMR (100 MHz, DMSO-d$_6$): δ 138.1, 134.0, 133.8, 128.7, 127.9, 127.0, 126.3, 124.4, 124.3, 122.5, 119.8, 118.8, 110.6, 110.5, 44.3, 31.9, 22.7, 19.4, 13.5; IR (ZnSe-ATR) 2962 (w), 2921 (w), 1469 (w), 1454 (w), 1360 (w), 1347 (w), 1196 (w), 1120 (w), 1042 (w), 819 (w), 757 (m), 743 (vs), 681 (w) cm$^{-1}$; Anal. Calcd for C$_{19}$H$_{19}$NS: C, 77.77; H, 6.53; N, 4.77; S, 10.93. Found: C, 77.74; H, 6.55; N, 4.81; S, 10.98.

(C) Synthesis of 11-alkyl-6,11-dihydrothiochromeno[4,3-b]indole 5-oxide (6a-6d)

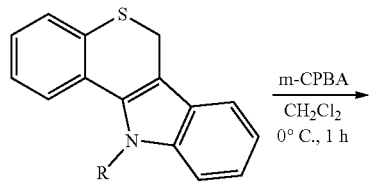

5a: R = Me
5b: R = Et
5c: R = n-Pr
5d: R = n-Bu

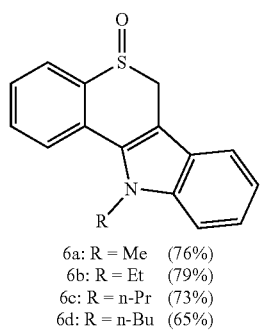

6a: R = Me (76%)
6b: R = Et (79%)
6c: R = n-Pr (73%)
6d: R = n-Bu (65%)

11-Alkyl-6,11-dihydrothiochromeno[4,3-b]indole (5a-5d, 1.0 equiv) was dissolved in anhydrous dichloromethane, after which m-chloroperbenzoic acid (69%, 1.1 equiv) was added thereto at 0° C. The resulting reaction mixture was stirred at 0 C for 1 hr and the reaction was terminated with the addition of a 20% sodium thiosulfate aqueous solution. The organic layer was separated and the remaining water layer was extracted three times with ethyl acetate. The combined organic layer was washed with a saturated sodium chloride aqueous solution, added with anhydrous sodium sulfate and filtered under reduced pressure. Thereafter, purification was conducted through the method described below.

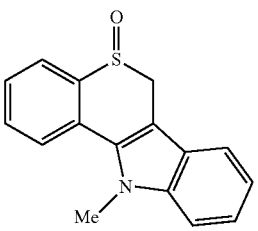

6a

11-Methyl-6,11-dihydrothiochromeno[4,3-b]indole 5-oxide (6a): The remaining solid was dispersed in diethyl ether:ethyl acetate at 8:1 (v/v) and then filtered, thus obtaining compound 6a as a yellow liquid. (76%): mp=180-183° C.; $R_f$=0.29 (EtOAc:hexane=1:1); $^1$H NMR (400 MHz, DMSO-d$_6$): δ 7.89 (d, J=7.6 Hz, 1H), 7.83 (d, J=7.2 Hz, 1H), 7.68-7.71 (m, 2H), 7.58-7.61 (m, 2H), 7.27 (dd, J=7.6, 7.2 Hz, 1H), 7.15 (dd, J=7.6, 7.2 Hz, 1H), 4.55 (d, J=14.2 Hz, 1H), 4.47 (d, J=14.2 Hz, 1H), 4.03 (s, 3H); $^{13}$C NMR (100 MHz, DMSO-d$_6$): δ 140.3, 138.6, 133.1, 131.5, 128.4, 127.0, 126.4, 125.9, 125.1, 123.2, 120.2, 119.1, 110.6, 100.7, 44.2, 32.3; IR (ZnSe-ATR) 2962 (w), 1581 (w), 1524 (w), 1468 (w), 1423 (w), 1356 (w), 1367 (w), 1261 (w), 1227 (w), 1123 (w), 1070 (m), 1048 (s), 1035 (s), 1025 (m), 1016 (m), 817 (w), 759 (vs), 667 (w) cm$^{-1}$; HRMS (m/z): [M+Na]$^+$ calcd for C$_{16}$H$_{13}$NNaOS, 290.0610; found, 290.0610.

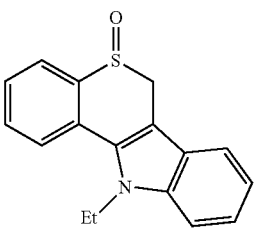

6b

11-Ethyl-6,11-dihydrothiochromeno[4,3-b]indole 5-oxide (6b): The remaining solid was dispersed in diethyl ether:ethyl acetate at 8:1 (v/v) and then filtered, thus obtaining compound 6b as a yellow liquid. (79%): mp=210-213 C; $R_f$=0.33 (EtOAc:hexane=1:1); $^1$H NMR (400 MHz, DMSO-d$_6$): δ 7.83 (d, J=7.6 Hz, 1H), 7.70-7.75 (m, 3H), 7.59-7.62 (m, 2H), 7.27 (dd, J=7.6, 7.2 Hz, 1H), 7.15 (dd, J=7.6, 7.2 Hz, 1H), 4.43-4.57 (m, 4H), 1.41 (t, J=7.0 Hz, 3H); $^{13}$C NMR (100 MHz, DMSO-d$_6$): δ 140.6, 137.8, 132.3, 131.7, 128.5, 127.0, 126.4, 126.2, 124.4, 123.2, 120.3, 119.2, 110.6, 101.1, 44.2, 15.32, 15.31; IR (ZnSe-ATR) 2974 (w), 1585 (w), 1459 (w), 1339 (w), 1159 (w), 1133 (w), 1075 (w), 1024 (m), 831 (w), 768 (w), 750 (vs), 737 (m), 700 (w), 668 (w) cm$^{-1}$; HRMS (m/z): [M+Na]$^+$ calcd for C$_{17}$H$_{15}$NNaOS, 304.0767; found, 304.0768.

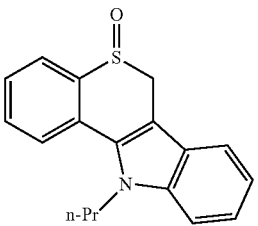

6c

11-Propyl-6,11-dihydrothiochromeno[4,3-b]indole 5-oxide (6c): The filtrate was purified through column chromatography (hexane:ethyl acetate=1:1), thus obtaining compound 6c as a yellow liquid. (80%): mp=128-132 C; $R_f$=0.27 (EtOAc:hexane=1:1); $^1$H NMR (400 MHz, DMSO-$d_6$): δ 7.82 (d, J=8.0 Hz, 1H), 7.69-7.77 (m, 3H), 7.58-7.64 (m, 2H), 7.26 (dd, J=7.6, 7.2 Hz, 1H), 7.15 (dd, J=7.6, 7.2 Hz, 1H), 4.56 (d, J=14.0 Hz, 1H), 4.42-4.46 (m, 3H), 1.77 (tq, J=7.4, 7.0 Hz, 2H), 0.84 (t, J=7.4 Hz, 3H); $^{13}$C NMR (100 MHz, DMSO-$d_6$): δ 140.6, 138.3, 132.6, 131.6, 128.5, 126.9, 126.6, 126.1, 124.4, 123.2, 120.3, 119.2, 110.9, 101.2, 45.8, 44.1, 23.2, 11.0; IR (ZnSe-ATR) 2958 (w), 1581 (w), 1481 (w), 1455 (w), 1410 (w), 1362 (w), 1209 (w), 1077 (m), 1056 (m), 1036 (m), 1024 (m), 902 (w), 763 (s), 753 (vs), 730 (m) cm$^{-1}$; HRMS (m/z): [M+Na]$^+$ calcd for $C_{18}H_{17}NNaOS$, 318.0923; found, 318.0925.

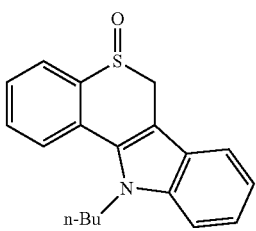

6d

11-Butyl-6,11-dihydrothiochromeno[4,3-b]indole 5-oxide (6d): Compound 6d was obtained as a yellow liquid through purification using column chromatography (hexane:ethyl acetate=1:1). (65%): mp=64-68 C; $R_f$=0.33 (EtOAc:hexane=1:1); $^1$H NMR (400 MHz, DMSO-$d_6$): δ 7.82 (d, J=7.2 Hz, 1H), 7.77 (d, J=7.6 Hz, 1H), 7.69-7.71 (m, 2H), 7.58-7.62 (m, 2H), 7.26 (dd, J=7.8, 7.6 Hz, 1H), 7.15 (dd, J=7.8, 7.6 Hz, 1H), 4.41-4.57 (m, 4H), 1.72 (tt, J=7.2, 7.2 Hz, 2H), 1.27 (tq, J=7.2, 7.2 Hz, 2H), 0.85 (t, J=7.2 Hz, 3H)); $^{13}$C NMR (100 MHz, DMSO-$d_6$): δ 140.7, 138.2, 132.6, 131.6, 128.5, 126.8, 126.6, 126.1, 124.3, 123.2, 120.3, 119.2, 110.9, 101.2, 44.2, 44.1, 31.8, 19.4, 13.5; IR (ZnSe-ATR) 2950 (w), 1585 (w), 1482 (w), 1456 (w), 1432 (w), 1349 (w), 1266 (w), 1131 (w), 1079 (m), 1052 (m), 1027 (m), 737 (s), 668 (w) cm$^{-1}$; HRMS (m/z): [M+Na]$^+$ calcd for $C_{19}H_{19}NNaOS$, 332.1080; found, 332.1080.

(D) Synthesis of thiochromeno[4,3-b]indol-5-ium 2,2,2-trifluoroacetate (7a-7d) from Compound 6 (Method A)

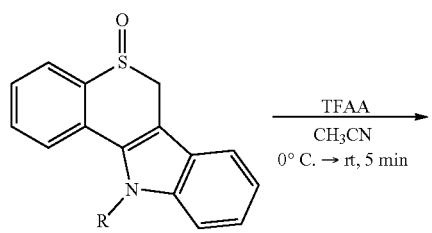

6a: R = Me
6b: R = Et
6c: R = n-Pr
6d: R = n-Bu

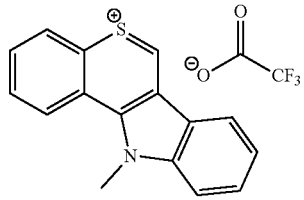

7a: R = Me
7b: R = Et
7c: R = n-Pr
7d: R = n-Bu

11-Alkyl-6,11-dihydrothiochromeno[4,3-b]indole 5-oxide (6a-6d, 1.0 equiv) was dispersed in acetonitrile in a nitrogen atmosphere, after which trifluoroacetic anhydride (3.0 equiv) was slowly added thereto at 0° C. The resulting reaction mixture was stirred at room temperature for 5 min, and the remaining reactant and the solvent were dried and removed under reduced pressure. The remaining solid was dispersed in anhydrous diethyl ether, cooled to 0° C., washed with cold diethyl ether, and filtered, thus obtaining sulfonium salts 7a-7d as deep yellow solids. These solids were used for the subsequent reaction without additional purification.

(E) Synthesis of thiochromeno[4,3-b]indol-5-ium 2,2,2-trifluoroacetate (7a-7d) from Compound 5 (Method B)

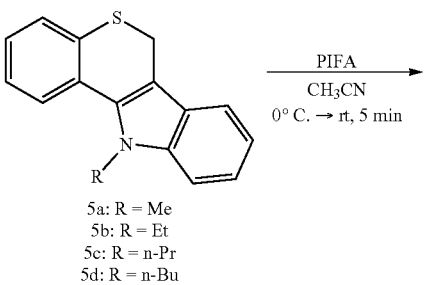

5a: R = Me
5b: R = Et
5c: R = n-Pr
5d: R = n-Bu

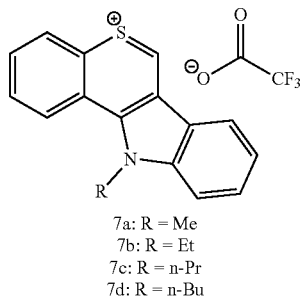

7a: R = Me
7b: R = Et
7c: R = n-Pr
7d: R = n-Bu

In a nitrogen atmosphere, 11-alkyl-6,11-dihydrothiochromeno[4,3-b]indole (5a-5d, 1.0 equiv) and bis(trifluoroacetoxy)iodobenzene (1.1 equiv) were mixed, after which anhydrous acetonitrile was added thereto at 0° C. The resulting reaction mixture was stirred at room temperature for 5 min, and the remaining reactant and the solvent were removed under reduced pressure. The remaining solid was dispersed in anhydrous diethyl ether, cooled to 0° C., washed with cold diethyl ether, and filtered, thus obtaining sulfonium salts 7a-7d as deep yellow solids. These solids were used for the subsequent reaction without additional purification.

(F) Synthesis of 2,5-dioxopyrrolidin-1-yl 3-((11-alkyl-6,11-dihydrothiochromeno[4,3-b]indol-6-yl)thio)propanoate (8a-8d)

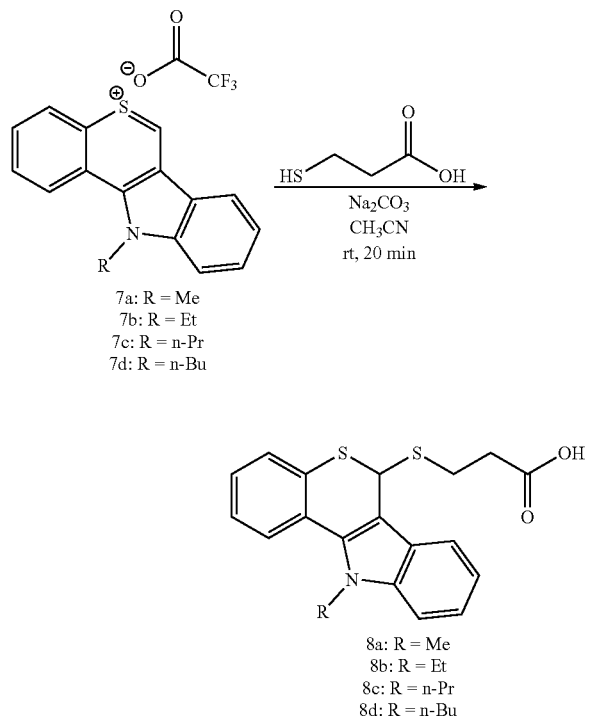

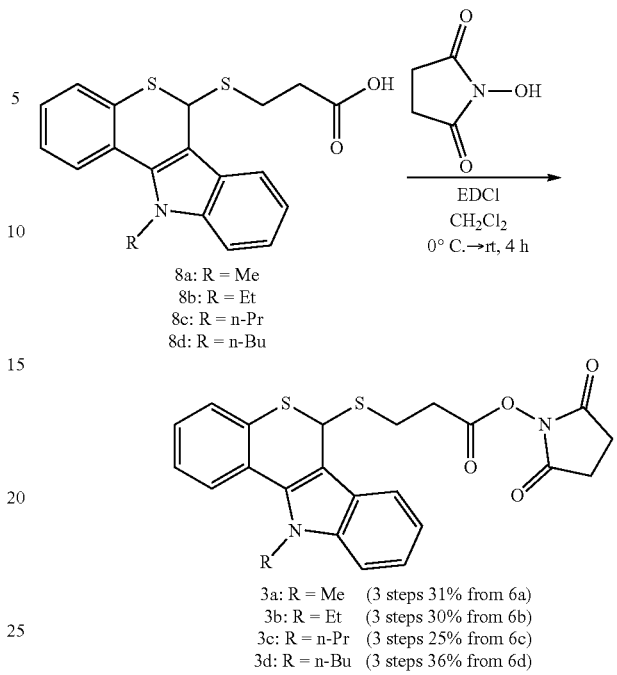

8a: R = Me
8b: R = Et
8c: R = n-Pr
8d: R = n-Bu

3a: R = Me   (3 steps 31% from 6a)
3b: R = Et   (3 steps 30% from 6b)
3c: R = n-Pr (3 steps 25% from 6c)
3d: R = n-Bu (3 steps 36% from 6d)

Each of sulfonium salts (7a-7d, 1.0 equiv) was dissolved in acetonitrile, after which 3-mercaptopropionic acid (1.0 equiv) and sodium carbonate (1.0 equiv) were sequentially added thereto. The resulting reaction mixture was stirred at room temperature (for about 20 min) until it was colorless, and was then diluted with ethyl acetate. Water was added until the remaining solid was completely dissolved, after which the organic layer was separated and the remaining water layer was extracted three times with ethyl acetate. The combined organic layer was washed with a saturated ammonium chloride aqueous solution and a saturated sodium chloride aqueous solution in sequence, added with anhydrous sodium sulfate and filtered under reduced pressure, after which the solvent of the filtrate was completely removed under reduced pressure, thus obtaining compounds 8a-8d as yellow solids. These solids were used for the subsequent reaction without additional purification.

Each of carboxylic acid compounds 8a-8d (1.0 equiv) and N-hydroxysuccinimide (1.1 equiv) were dissolved in anhydrous dichloromethane in a nitrogen atmosphere. The resulting reaction mixture was added with a solution of N-(3-dimethylaminopropyl)-N'-ethylcarbodiimide hydrochloride (3.0 equiv) separately dissolved in anhydrous dichloromethane. The reaction mixture was stirred at room temperature for 4 hr and then diluted with dichloromethane. The resulting solution was washed two times with water, added with anhydrous sodium sulfate and filtered under reduced pressure. The solvent of the filtrate was completely removed under reduced pressure and then purified through column chromatography (hexane:ethyl acetate=1:1), thus obtaining compounds 3a-3d as white solids.

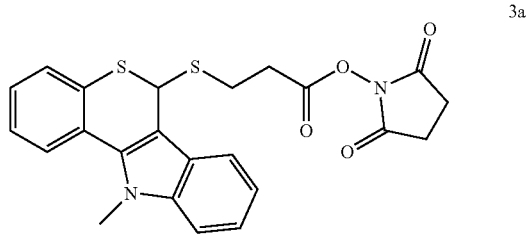 [SMILES: Cn1c2c(c3ccccc31)C(SCCC(=O)ON1C(=O)CCC1=O)Sc1ccccc1-2]

3a 2,5-Dioxopyrrolidin-1-yl 3-((11-methyl-6,11-dihydrothiochromeno[4,3-b]indol-6-yl)thio)propanoate (3a): 31% (yield synthesized from compound 6a using Methods A1 and B); mp=90-96° C. dec; $R_f$=0.52 (EtOAc:hexane=1:1); $^1$H NMR (400 MHz, DMSO-$d_6$): δ 7.98 (d, J=8.0 Hz, 1H), 7.71 (d, J=8.0 Hz, 1H), 7.59 (d, J=7.6 Hz, 1H), 7.56 (d, J=8.4 Hz, 1H), 7.42 (dd, J=8.0, 7.2 Hz, 1H), 7.33 (dd, J=7.6, 7.2 Hz, 1H), 7.27 (dd, J=8.4, 7.2 Hz, 1H), 7.15 (dd, J=7.6, 7.2 Hz, 1H), 6.23 (s, 1H), 4.00 (s, 3H), 3.10-3.24 (m, 2H), 2.96-3.03 (m, 1H), 2.75-2.82 (m, 5H); $^{13}$C NMR (100 MHz, DMSO-$d_6$): d 170.2, 168.0, 138.2, 134.7, 130.5, 129.7, 127.7, 126.8, 126.7, 125.1, 123.0, 122.7, 120.2, 118.7, 110.7, 110.4, 42.9, 33.0, 31.5, 25.7, 25.5; IR (ZnSe-ATR) 1811 (w), 1782 (w), 1732 (s), 1470 (w), 1426 (w), 1361 (w), 1201 (m), 1064 (m), 824 (w), 743 (s), 668 (w) cm$^{-1}$; Anal. Calcd for C$_{23}$H$_{20}$N$_2$O$_4$S$_2$: C, 61.04; H, 4.45; N, 6.19; S, 14.17. Found: C, 61.14; H, 4.48; N, 6.10 S, 14.04.

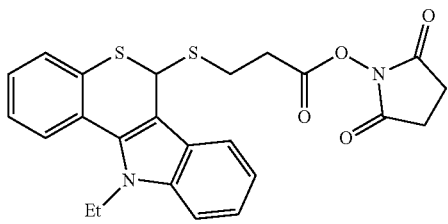

3b 2,5-Dioxopyrrolidin-1-yl 3-((11-ethyl-6,11-dihydrothiochromeno[4,3-b]indol-6-yl)thio)propanoate (3b): 30% (yield synthesized from compound 6b using Methods A1 and B); mp=82-87° C. dec; R$_f$=0.32 (EtOAc:hexane=1:1); $^1$H NMR (400 MHz, DMSO-d$_6$): δ 7.81 (d, J=8.0 Hz, 1H), 7.71 (d, J=8.0 Hz, 1H), 7.60 (d, J=7.2 Hz, 1H), 7.58 (d, J=8.0 Hz, 1H), 7.44 (dd, J=7.6, 7.6 Hz, 1H), 7.33 (dd, J=7.6, 7.6 Hz, 1H), 7.27 (dd, J=7.6, 7.6 Hz, 1H), 7.16 (dd, J=7.6, 7.2 Hz, 1H), 6.21 (s, 1H), 4.44 (q, J=7.0 Hz, 2H), 3.08-3.23 (m, 2H), 2.96-3.03 (m, 1H), 2.75-2.82 (m, 5H), 1.42 (t, J=7.0 Hz, 3H); $^{13}$C NMR (100 MHz, DMSO-d$_6$): δ 170.1, 167.9, 137.5, 133.9, 130.6, 129.9, 127.6, 126.9, 126.7, 124.4, 123.1, 123.0, 120.3, 118.8, 111.2, 110.4, 42.8, 31.5, 25.7, 25.5, 15.4; IR (ZnSe-ATR) 1810 (w), 1781 (w), 1733 (s), 1459 (w), 1426 (w), 1345 (w), 1203 (m), 1066 (m), 1044 (m), 991 (w), 813 (w), 745 (vs) cm$^{-1}$; Anal. Calcd for C$_{24}$H$_{22}$N$_2$O$_4$S$_2$: C, 61.78; H, 4.75; N, 6.00; S, 13.74. Found: C, 61.83; H, 4.79; N, 5.97 S, 13.91.

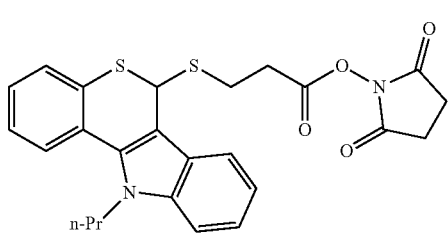

3c 2,5-Dioxopyrrolidin-1-yl 3-((11-propyl-6,11-dihydrothiochromeno[4,3-b]indol-6-yl)thio)propanoate (3c): 25% (yield synthesized from compound 6c using Methods A1 and B); 32% (yield synthesized from compound 5c using Methods A2 and B); mp=77-82° C. dec; R$_f$=0.36 (EtOAc:hexane=1:1); $^1$H NMR (400 MHz, DMSO-d$_6$): δ 7.83 (d, J=8.0 Hz, 1H), 7.70 (d, J=8.0 Hz, 1H), 7.59 (d, J=7.6 Hz, 2H), 7.43 (dd, J=7.6, 7.6 Hz, 1H), 7.32 (dd, J=7.6, 7.6 Hz, 1H), 7.26 (dd, J=8.0, 7.2 Hz, 1H), 7.15 (dd, J=8.0, 7.2 Hz, 1H), 6.21 (s, 1H), 4.31-4.46 (m, 2H), 3.08-3.21 (m, 2H), 2.96-3.03 (m, 1H), 2.75-2.82 (m, 5H), 1.67-1.82 (m, 2H), 0.83 (t, J=7.2 Hz, 3H); $^{13}$C NMR (100 MHz, DMSO-d$_6$): δ 170.1, 167.9, 138.0, 134.1, 130.5, 129.9, 127.6, 126.89, 126.90, 124.3, 123.0, 122.9, 120.2, 118.8, 111.5, 110.7, 46.3, 42.7, 31.4, 25.7, 25.5, 23.1, 10.9; IR (ZnSe-ATR) 2961 (w), 1812 (w), 1783 (w), 1733 (s), 1460 (w), 1424 (w), 1348 (w), 1201 (m), 1065 (m), 1045 (m), 908 (w), 810 (w), 744 (vs) cm$^{-1}$; Anal. Calcd for C$_{25}$H$_{24}$N$_2$O$_4$S$_2$: C, 62.48; H, 5.03; N, 5.83; S, 13.34. Found: C, 62.42; H, 5.03; N, 5.82 S, 13.40.

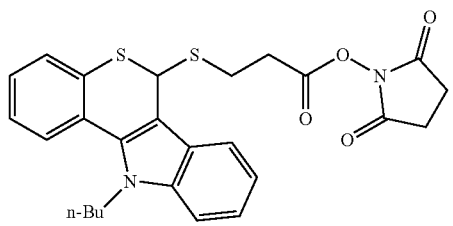

3d 2,5-Dioxopyrrolidin-1-yl 3-((11-butyl-6, 11-dihydrothiochromeno[4,3-b]indol-6-yl)thio)propanoate (3d): 36% (yield synthesized from compound 6d using Methods A1 and B); mp=76-81° C. dec; R$_f$=0.35 (EtOAc:hexane=1:1); $^1$H NMR (400 MHz, DMSO-d6): d 7.85 (d, J=8.0 Hz, 1H), 7.70 (d, J=8.0 Hz, 1H), 7.58-7.60 (m, 2H), 7.43 (dd, J=8.0, 8.0 Hz, 1H), 7.32 (dd, J=8.0, 7.2 Hz, 1H), 7.26 (dd, J=7.6, 7.2 Hz, 1H), 7.15 (dd, J=7.6, 7.2 Hz, 1H), 6.21 (s, 1H), 4.40-4.46 (m, 2H), 3.08-3.21 (m, 2H), 2.96-3.03 (m, 1H), 2.77-2.82 (m, 5H), 1.65-1.75 (m, 2H), 1.21-1.29 (m, 2H), 0.86 (t, J=7.0 Hz, 3H); $^{13}$C NMR (100 MHz, DMSO-d6): δ 170.1, 167.9, 137.9, 134.2, 130.5, 129.9, 127.6, 126.9, 126.8, 124.3, 123.03, 122.96, 120.2, 118.8, 111.5, 110.6, 44.5, 42.8, 31.8, 31.4, 25.7, 25.5, 19.3, 13.5; IR (ZnSe-ATR) 2954 (w), 2925 (w), 1811 (w), 1783 (w), 1735 (s), 1459 (w), 1422 (w), 1359 (w), 1200 (m), 1066 (m), 1042 (w), 810 (w), 745 (s), 669 (m) cm$^{-1}$; Anal. Calcd for C$_{26}$H$_{26}$N$_2$O$_4$S$_2$: C, 63.14; H, 5.30; N, 5.66; S, 12.96. Found: C, 63.14; H, 5.30; N, 5.69 S, 12.90.

Example 2: Synthesis of Mass Tag (II)

Synthesis of sodium 1-((3-((11-methyl-6,11-dihydrothiochromeno[4,3-b]indol-6-yl)thio)propanoyl)oxy)-2,5-dioxopyrrolidine-3-sulfonate (9)

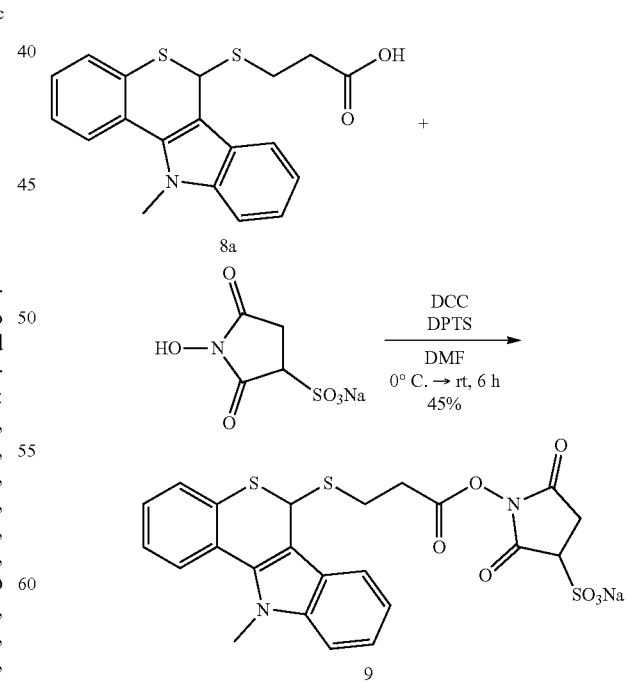

3-((11-Methyl-6, 11-dihydrothiochromeno[4,3-b]indol-6-yl)thio)propanoic acid (8a, 0.015 g, 0.042 mmol), N-hydroxysulfosuccinimide sodium salt (0.009 g, 0.04 mmol), and N,N-dimethylpyridinium, p-toluenesulfonate (DPTS) (0.001 g, 0.004 mmol) were dissolved in anhydrous dimethylformamide (0.3 mL) in a nitrogen atmosphere and then cooled to 0° C. The resulting reaction mixture was slowly added with a solution of N,N-dicyclohexylcarbodiimide (0.010 g, 0.051 mmol) separately dissolved in anhydrous dichloromethane (0.3 mL) in a nitrogen atmosphere. The temperature of the reaction mixture was gradually elevated to room temperature and stirred. After 6 hr, the reaction mixture was cooled to 0° C. and the precipitated solid was filtered under reduced pressure and washed with cold dichloromethane. The solvent of the filtrate was completely removed under reduced pressure, thus obtaining compound 9 as a yellow solid. (45%): $^1$H NMR (400 MHz, DMSO-d6): d 7.98 (d, J=7.6 Hz, 1H), 7.10 (d, J=7.6 Hz, 1H), 7.60 (d, J=7.6 Hz, 1H), 7.55 (d, J=8.4 Hz, 1H), 7.41 (dd, J=7.6, 7.6 Hz, 1H), 7.33 (dd, J=8.4, 7.2 Hz, 1H), 7.27 (dd, J=7.6, 7.2 Hz, 1H), 7.16 (dd, J=7.6, 7.2 Hz, 1H), 6.24 (s, 1H), 4.00 (s, 3H), 3.13-3.19 (m, 4H), 2.94-3.02 (m, 1H), 2.76-2.83 (m, 1H).

Example 3: Synthesis of Mass Tag (III)

Synthesis of perfluorophenyl 3-((11-methyl-6, 11-dihydrothiochromeno[4,3-b]indol-6-yl)thio)propanoate (10)

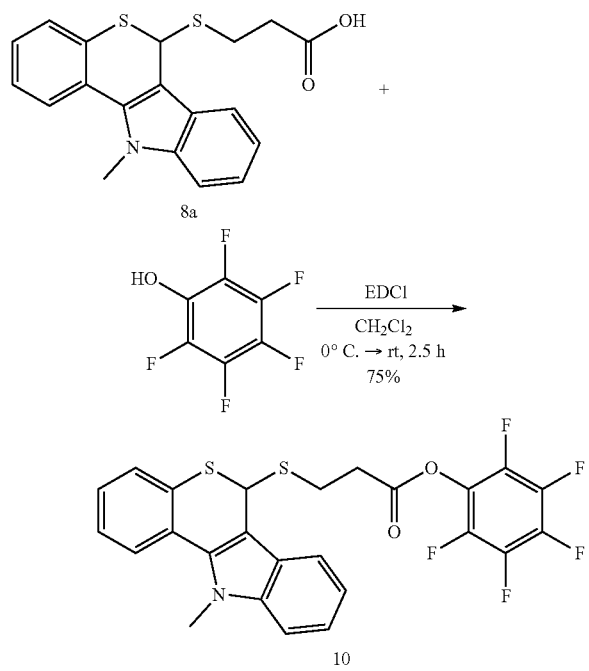

3-((11-Methyl-6, 11-dihydrothiochromeno[4,3-b]indol-6-yl)thio)propanoic acid (8a, 0.020 g, 0.056 mmol) and pentafluorophenol (0.011 mg, 0.062 mmol) were dissolved in anhydrous dichloromethane (0.7 mL) in a nitrogen atmosphere. The resulting reaction mixture was added with a solution of N-(3-dimethylaminopropyl)-N'-ethylcarbodiimide hydrochloride (0.032 mg, 0.017 mmol) separately dissolved in anhydrous dichloromethane (0.3 mL). The resulting reaction mixture was stirred at room temperature for 2.5 hr and then diluted with dichloromethane (3 mL). The resulting solution was washed two times with water (3 mL), added with anhydrous sodium sulfate and filtered under reduced pressure. The solvent of the filtrate was completely removed under reduced pressure, followed by purification through column chromatography (hexane:ethyl acetate=9:1), thus obtaining compound 10 as a yellow solid. (75%): $^1$H NMR (400 MHz, DMSO-d6): δ 7.98 (d, J=8.0 Hz, 1H), 7.67 (d, J=8.4 Hz, 1H), 7.55-7.59 (m, 2H), 7.41 (dd, J=6.8, 6.8 Hz, 1H), 7.33 (dd, J=7.2, 7.2 Hz, 1H), 7.27 (dd, J=8.4, 7.2 Hz, 1H), 7.14 (dd, J=7.2, 6.8 Hz, 1H), 6.25 (s, 1H), 4.00 (s, 3H), 3.27-3.33 (m, 2H), 2.99-3.02 (m, 1H), 2.83-2.88 (m, 1H).

Example 4: Synthesis of Mass Tag (IV)

Synthesis of sodium 2,3,5,6-tetrafluoro-4-((3-((11-methyl-6, 11-dihydrothiochromeno[4,3-b]indol-6-yl)thio)propanoyl)oxy)benzenesulfonate (11)

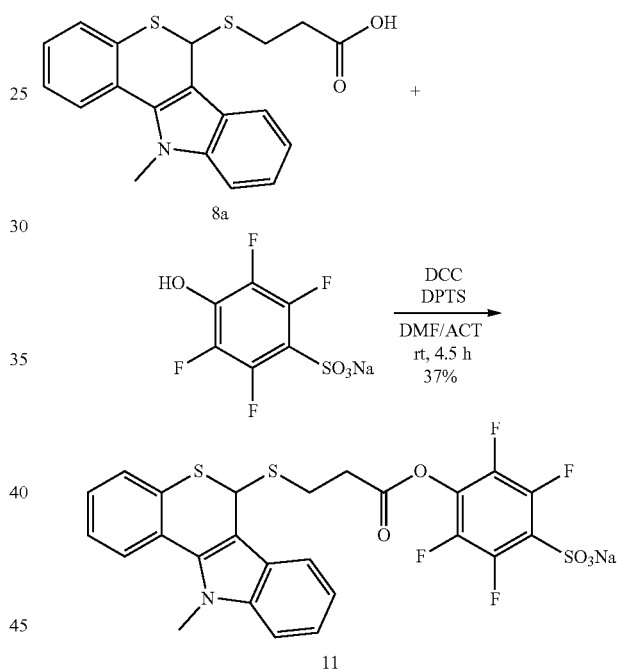

3-((11-Methyl-6, 11-dihydrothiochromeno[4,3-b]indol-6-yl)thio)propanoic acid (8a, 0.050 g, 0.14 mmol), sodium 2,3,5,6-tetrafluoro-4-hydroxybenzenesulfonate (0.038 g, 0.14 mmol), and N,N-dimethylpyridinium p-toluenesulfonate (DPTS) (0.002 g, 0.007 mmol) were dissolved in anhydrous acetone/anhydrous dimethylformamide (v:v=15:1, 3.0 mL) in a nitrogen atmosphere and then cooled to 0° C. The resulting reaction mixture was slowly added with a solution of N,N'-dicyclohexylcarbodiimide (0.035 g, 0.17 mmol) dissolved in anhydrous acetone (1.0 mL) in a nitrogen atmosphere. The temperature of the reaction mixture was gradually elevated to room temperature and stirred for 4.5 hr. The reaction mixture was cooled to 0° C., after which the precipitated solid was filtered under reduced pressure and washed with cold dichloromethane. The solvent of the filtrate was completely removed under reduced pressure, followed by purification through column chromatography (dichloromethane:acetone=3:7), thus obtaining compound 11 as a yellow solid. (37%): $^1$H NMR (400 MHz, DMSO-d6): δ 7.98 (d, J=8.0 Hz, 1H), 7.67 (d, J=7.2 Hz, 1H), 7.55-7.60 (m, 2H), 7.41 (dd, J=7.2, 7.2 Hz, 1H), 7.32 (dd, J=8.0, 7.2 Hz, 1H), 7.27 (dd, J=7.6, 7.2 Hz, 1H), 7.14 (dd, J=7.6, 7.2 Hz, 1H), 6.25 (s, 1H), 4.00 (s, 3H), 3.20-3.34 (m, 2H), 2.96-3.03 (m, 1H), 2.80-2.89 (m, 1H).

Example 5: Solubility Comparison of Compounds 1, 2, 3a

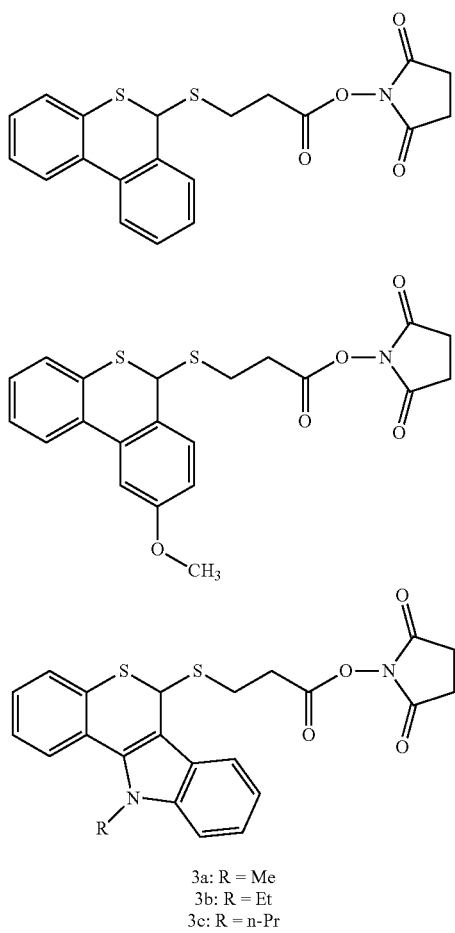

Figure 5:
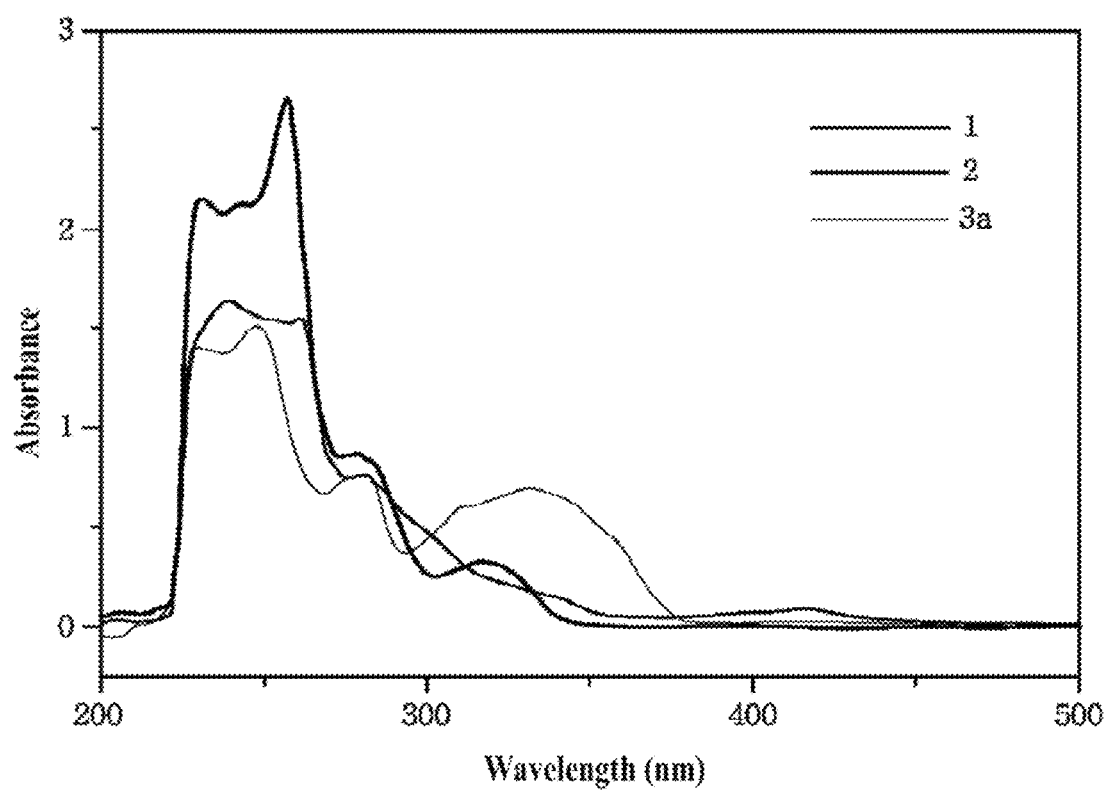
Figure 6:
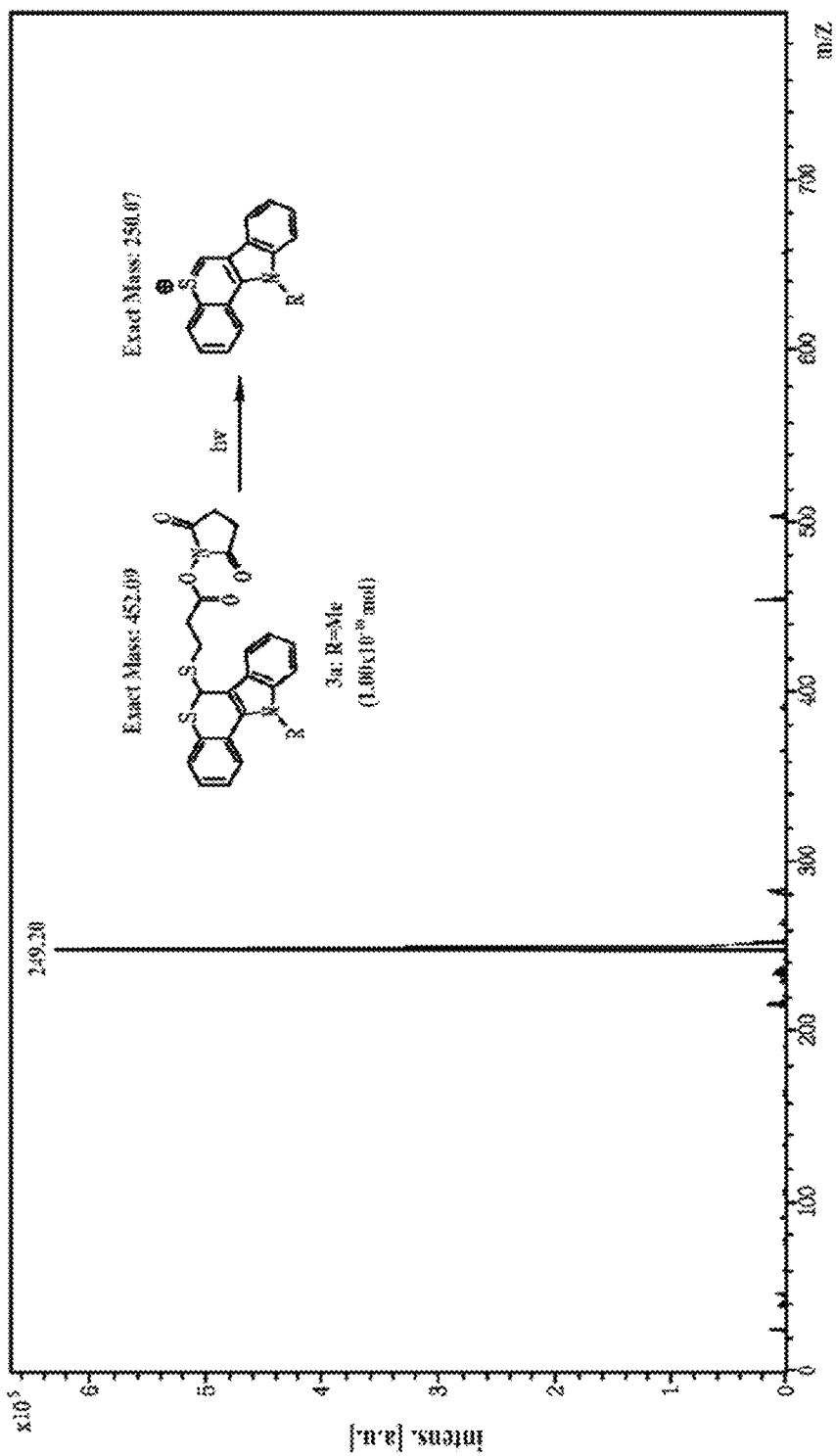
FIG. 6 shows the mass spectrometry spectrum results of compound 3a obtained through matrix-less LDI-TOF MS.

As shown in FIGS. 5 and 6, indole-introduced derivative 3a exhibited high absorbance at 355 nm compared to compounds 1 and 2, resulting in very effective ionization through laser irradiation.

Indole-introduced derivative 3 was remarkably improved in solubility compared to existing ferrocene derivative mass tags. For example, the ferrocene derivative formed a cloud point when 10% water was added upon dissolution in DMSO, whereas indole-introduced 2-alkylthio-2H-thiochromene derivative 3a did not form a cloud point until 30% water was added.

Example 6: Matrix-Less LDI MS Spectrum

A) Matrix-Less LDI-TOF Test of Photocleavable Mass Tag or Biomaterial Tagged Therewith A photocleavable mass tag or a biomaterial tagged therewith was dissolved in tetrahydrofuran, and 1.0 μL thereof was dropped on each spot of a plate and exposed in air at room temperature, thereby drying the solvent The dried sample on the plate was analyzed using a MALDI-TOF mass spectrometer (Autoflex Speed series, Bruker Daltonics, Leipzig, Germany). All spectra were measured in a positive reflectron mode. The mass range was set to 0-800 Da, and data analysis was performed using flexAnalysis software.

B) Martrix-Less LDI MS Spectrum of Mass Tag 3a-3d

Figure 7:
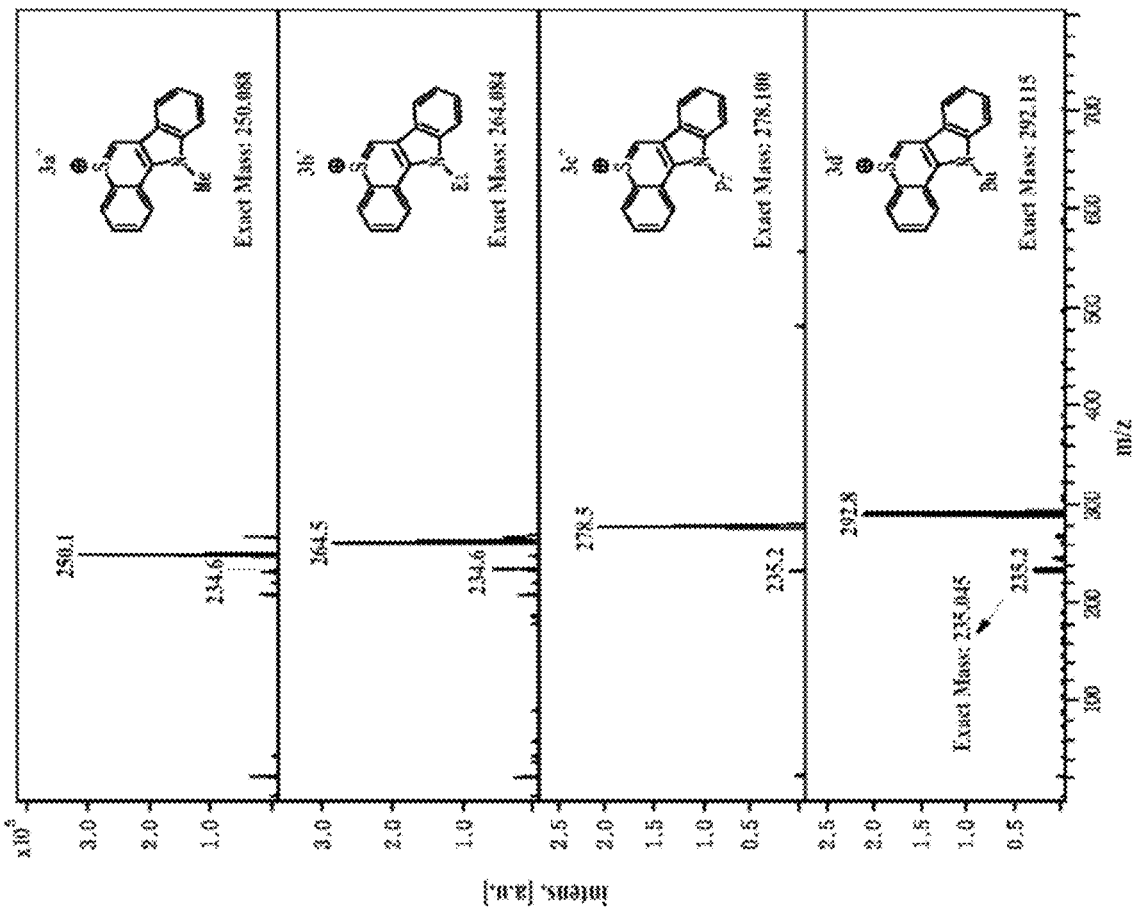
FIG. 7 shows the matrix-less LDI MS spectrum results of mass tags 3a-3d.
Figure 7:
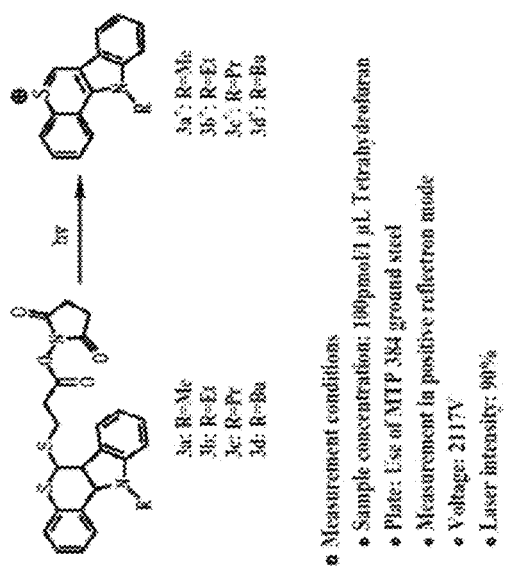

The matrix-less LDI MS spectra of mass tags 3a-3d are shown in FIG. 7. In matrix-less LDI-TOF MS, a desired photocleavage reaction occurred and thus peaks corresponding to respective cations were detected at high intensity. Here, a peak at about 235 m/z was observed in common, which means that some mass-changing group was detached during the photocleavage. The detached proportion thereof is very low and thus it is not expected to cause a big problem when actually applied to marker detection.

Example 7: Matrix-Less LDI MS Sensitivity Comparison

The sensitivity at which the novel photocleavable mass tag is detected in matrix-less LDI-TOF MS was compared with that of the conventionally known tag.

Figure 8:
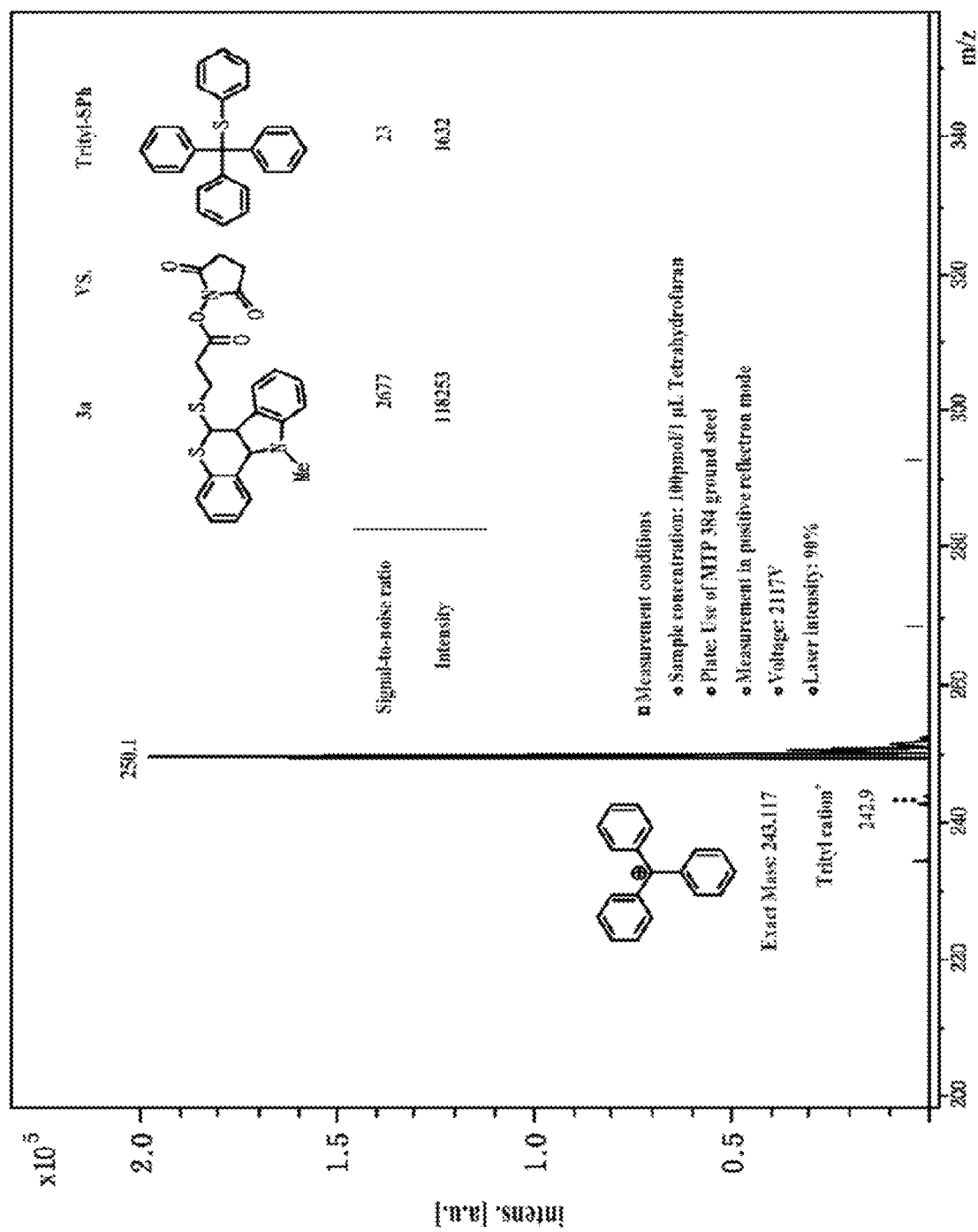
FIG. 8 shows the comparison results of matrix-less LDI MS sensitivity of compound 3a, which is the mass tag of the present invention, and a conventionally known trityl-SPh derivative.

A trityl tag (trityl-SPh), which is one of the photocleavable tags reported in existing documents, and compound 3a of the present invention were added in the same amount and analyzed. The results are shown in FIG. 8. As shown in FIG. 8, the tag 3a exhibited sensitivity and a signal-to-noise ratio as high as about 110 times those of the trityl tag.

Figure 9:
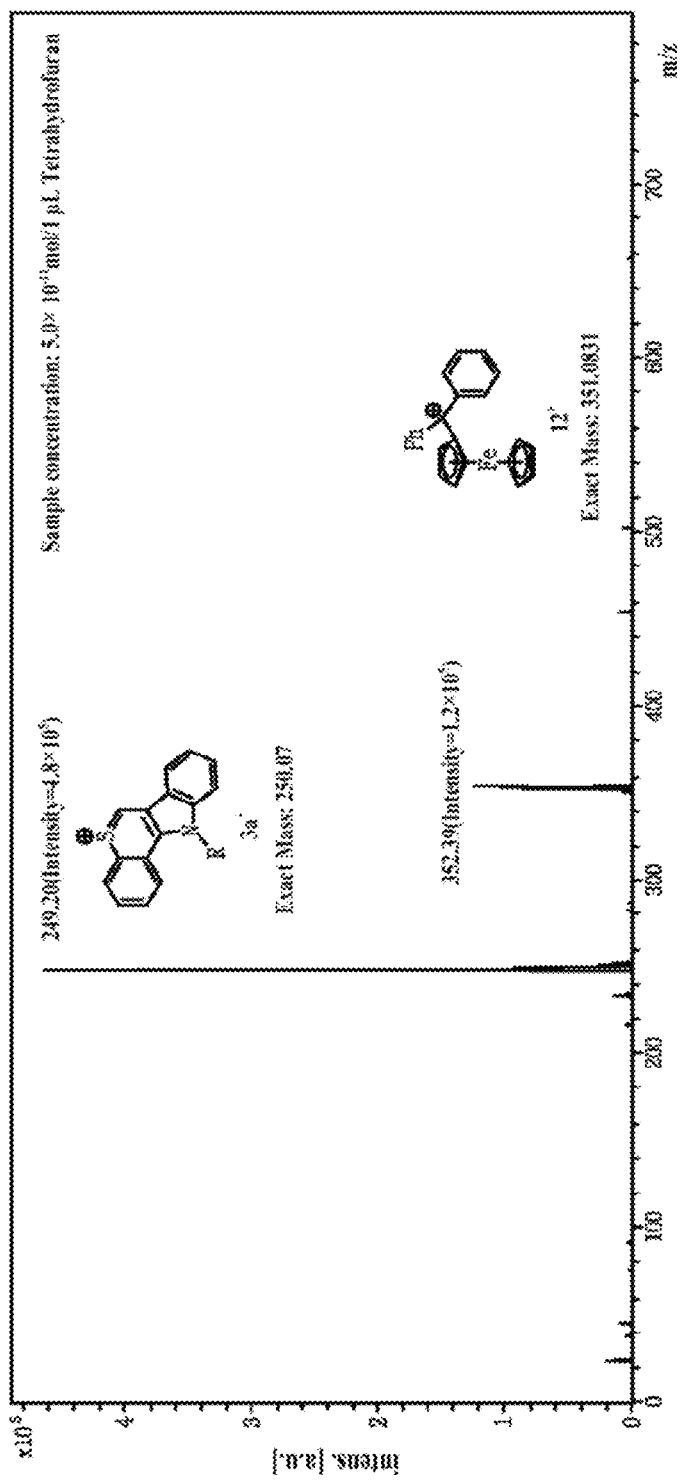
FIG. 9 shows the comparison results of matrix-less LDI MS sensitivity of compound 3a, which is the mass tag of the present invention, and a ferrocene-based mass tag disclosed in the related art.

Furthermore, the results of matrix-less LDI MS sensitivity comparison thereof with the ferrocene-based tag disclosed in the related patent (Korean Patent Application No. 10-2014-0050964) are shown in FIG. 9. As shown in FIG. 9, the tag according to the present invention exhibited higher detection intensity by about 4 times. Therefore, the tag of the present invention can be concluded to be a mass tag having remarkably high sensitivity compared to conventionally known tags.

Example 8: Detection Limit of Mass Tag

Figure 10:
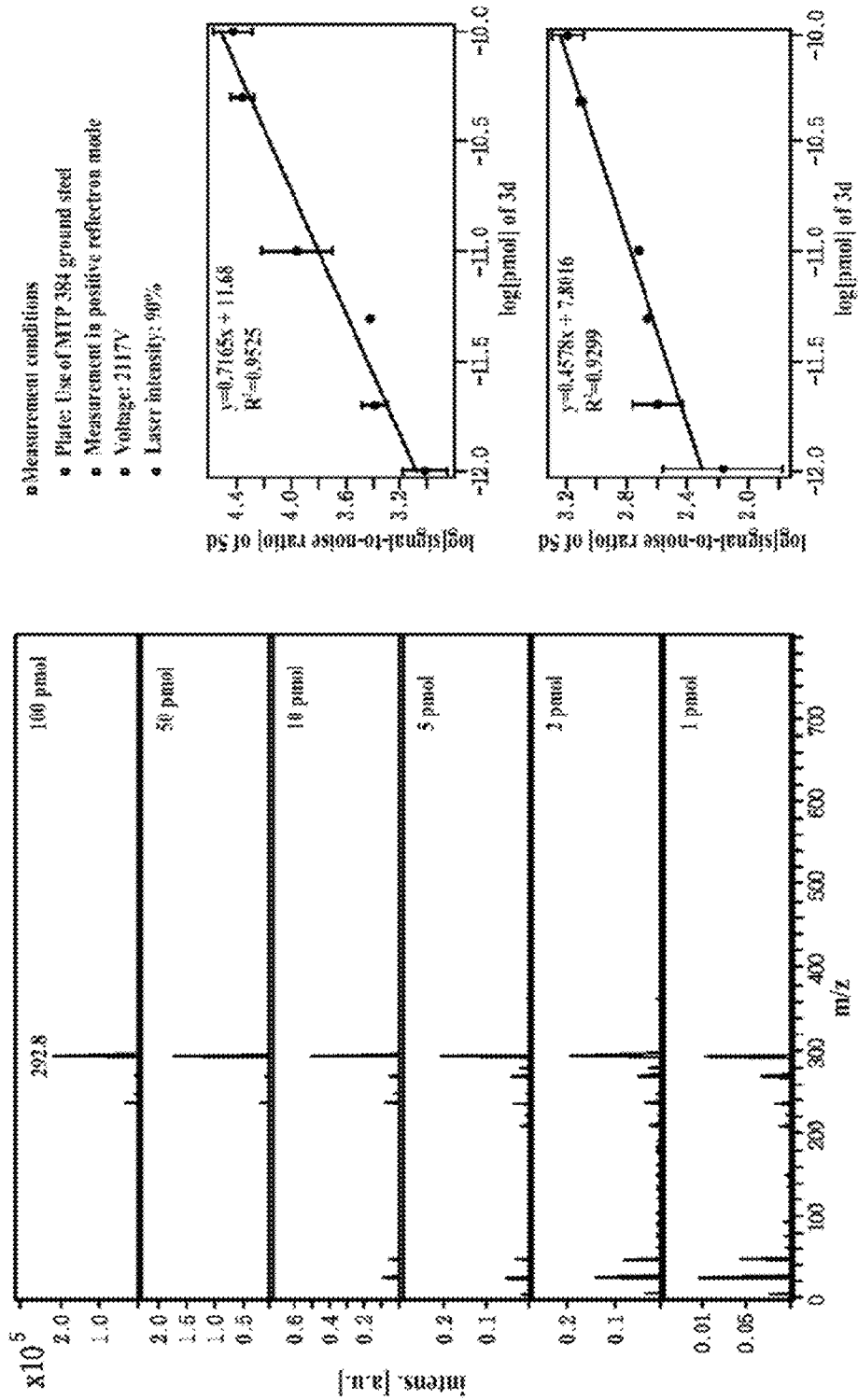
FIG. 10 shows the test data for detection limit of the mass tag 3d of the present invention upon matrix-less LDI MS.

In order to evaluate the minimum detection limit of the novel mass tag, a test for determining the minimum sample content in matrix-less LDI-TOF MS was performed. The tags of 100/50/10/5/2/1 pmol were loaded on MALDI measurement plates and spectrum results thereof were compared. Based on the results in which the peak area and the signal-to-noise ratio (S/N ratio) were represented depending on molar amounts, linear graphs were obtained in all of tags 3a, 3b, 3c, 3d, as shown in FIG. 10 (typically only posted data for 3d).

This suggests that the present analysis method is applicable to the quantitative analysis of biomarkers. The minimum amount of the tag that may be reproducibly detected was measured to be 1 pmol, at which the signal-to-noise ratio was measured to be about 100. The cation was detected even in lower molar amounts, but the difference in detection intensity was found to be significant depending on the measurement position on the spot of the plate. This is interpreted as a phenomenon that occurs because the tag does not spread evenly and is crystallized and agglomerated only in a portion thereof owing to the high crystallinity of the tag. However, conjugation of the tag to the antibody may weaken the crystallinity so that the tag may be evenly distributed within the spot, and therefore the minimum detection limit thereof is deemed to be sufficiently improved.

The invention claimed is:

1. A compound represented by Formula I below:

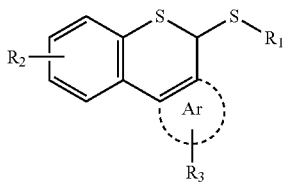

(Formula I)

In Formula I, $R_1$ is a C1-12 alkyl group, a C6-60 aryl group, or a C2-60 heteroaryl group containing at least one heteroatom selected from among N, S and O, having a reactive group at a terminal thereof, the reactive group being any one of a N-hydroxysuccinimide ester group, a N-hydroxysulfosuccinimide ester group, a pentafluorophenyl ester group, a 4-sulfo-2,3,5,6-tetrafluorophenyl ester group, a nitrophenyl ester group, a 2,4,5-trichlorophenyl ester group, a phthalimido ester group, a N-hydroxy-5-norbornen-endo-2,3-dicarboimide ester group, and a maleimide group, $R_2$ and $R_3$ are independently hydrogen, a C1-12 alkyl, a C6-60 aryl, a C1-12 alkoxy, a C1-12 alkylamino, a C1-12 alkylthio or a fused ring, the fused ring being any one selected from among pyrrole, thiophene, indole, furan, imidazole, triazole, diazole, and pyrimidine, and Ar is benzene or a heteroaromatic ring selected from among pyrrole, thiophene, indole, furan, imidazole, triazole, diazole, and pyrimidine.

2. A compound represented by Formula II below:

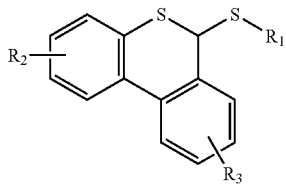

(Formula II)

in Formula II, $R_1$ is a C1-12 alkyl group, a C6-60 aryl group, or a C2-60 heteroaryl group containing at least one heteroatom selected from among N, S and O, having a reactive group at a terminal thereof, the reactive group being any one of a N-hydroxysuccinimide ester group, a N-hydroxysulfosuccinimide ester group, a pentafluorophenyl ester group, a 4-sulfo-2,3,5,6-tetrafluorophenyl ester group, a nitrophenyl ester group, a 2,4,5-trichlorophenyl ester group, a phthalimido ester group, a N-hydroxy-5-norbornen-endo-2,3-dicarboimide ester group, and a maleimide group, and $R_2$ and $R_3$ are independently hydrogen, a C1-12 alkyl, a C6-60 aryl, a C1-12 alkoxy, a C1-12 alkylamino, a C1-12 alkylthio or a fused ring, the fused ring being any one selected from among pyrrole, thiophene, indole, furan, imidazole, triazole, diazole, and pyrimidine.

3. A compound represented by Formula III below:

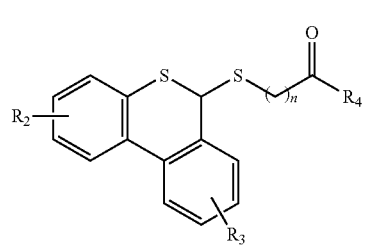

(Formula III)

in Formula III, $R_2$ and $R_3$ are independently hydrogen, a C1-12 alkyl, a C6-60 aryl, a C1-12 alkoxy, a C1-12 alkylamino, a C1-12 alkylthio or a fused ring, $C(=O)R_4$ is N-hydroxysuccinimidyl, N-hydroxy sulfosuccinimidyl, pentafluorophenyloxy, 4-sulfo-2,3,5,6-tetrafluorophenyloxy, nitrophenyloxy, 2,4,5-trichlorophenyloxy, phthalimidoyloxy, N-hydroxy-5-norbornen-endo-2,3-dicarboimidyloxy, or maleimide, and n is an integer of 1-12, the fused ring being any one selected from among pyrrole, thiophene, indole, furan, imidazole, triazole, diazole, and pyrimidine.

4. A compound represented by Formula IV below:

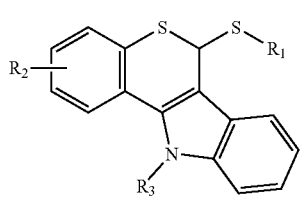

(Formula IV)

in Formula IV, $R_1$ is a C1-12 alkyl group, a C6-60 aryl group, or a C2-60 heteroaryl group containing at least one heteroatom selected from among N, S and O, having a reactive group at a terminal thereof, the reactive group being any one of a N-hydroxysuccinimide ester group, a N-hydroxysulfosuccinimide ester group, a pentafluorophenyl ester group, a 4-sulfo-2,3,5,6-tetrafluorophenyl ester group, a nitrophenyl ester group, a 2,4,5-trichlorophenyl ester group, a phthalimido ester group, a N-hydroxy-5-norbornen-endo-2,3-dicarboimide ester group, and a maleimide group, and $R_2$ and $R_3$ are independently hydrogen, a C1-12 alkyl, a C6-60 aryl, a C1-12 alkoxy, a C1-12 alkylamino, a C1-12 alkylthio or a fused ring, the fused ring being any one selected from among pyrrole, thiophene, indole, furan, imidazole, triazole, diazole, and pyrimidine.

5. A compound represented by Formula V below:

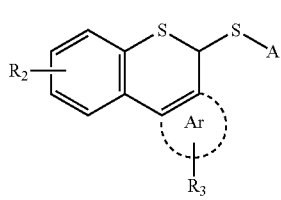

(Formula V)

in Formula V, A is a C1-12 alkyl group, a C6-60 aryl group, or a C2-60 heteroaryl group containing at least one heteroatom selected from among N, S and O, having a reactive group at a terminal thereof, the reactive group being any one of a N-hydroxysuccinimide ester group, a N-hydroxysulfosuccinimide ester group, a pentafluorophenyl ester group, a 4-sulfo-2,3,5,6-tetrafluorophenyl ester group, a nitrophenyl ester group, a 2,4,5-trichlorophenyl ester group, a phthalimido ester group, a N-hydroxy-5-norbornen-endo-2,3-dicarboimide ester group, and a maleimide group, $R_2$ and $R_3$ are independently hydrogen, a C1-12 alkyl, a C6-60 aryl, a C1-12 alkoxy, a C1-12 alkylamino, a C1-12 alkylthio or a fused ring, the fused ring being any one selected from among pyrrole, thiophene, indole, furan, imidazole, triazole, diazole, and pyrimidine, and Ar is benzene or a heteroaromatic ring selected from among pyrrole, thiophene, indole, furan, imidazole, triazole, diazole, and pyrimidine.

6. The compound of any one of claims 1 to 5, which is used for MALDI-TOF (Matrix-Assisted Laser Desorption/Ionization Time-Of-Flight) mass spectrometry or matrix-less LDI-TOF (Laser Desorption/Ionization Time-Of-Flight) mass spectrometry.

7. A conjugate compound of a biomaterial and a compound represented by Formula Ia below:

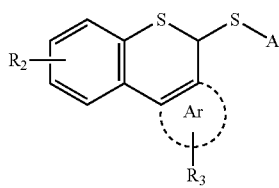

(Formula Ia)

in Formula Ia, A is a C1-12 alkyl group, a C6-60 aryl group, or a C2-60 heteroaryl group containing at least one heteroatom selected from among N, S and O, having a reactive group at a terminal thereof, the reactive group being any one of a N-hydroxysuccinimide ester group, a N-hydroxysulfosuccinimide ester group, a pentafluorophenyl ester group, a 4-sulfo-2,3,5,6-tetrafluorophenyl ester group, a nitrophenyl ester group, a 2,4,5-trichlorophenyl ester group, a phthalimido ester group, a N-hydroxy-5-norbornen-endo-2,3-dicarboimide ester group, and a maleimide group, $R_2$ and $R_3$ are independently hydrogen, a C1-12 alkyl, a C6-60 aryl, a C1-12 alkoxy, a C1-12 alkylamino, a C1-12 alkylthio or a fused ring, the fused ring being any one selected from among pyrrole, thiophene, indole, furan, imidazole, triazole, diazole, and pyrimidine, and Ar is benzene or a heteroaromatic ring selected from among pyrrole, thiophene, indole, imidazole, triazole, and pyrimidine, wherein the biomaterial is an antigen, an antibody, a biomarker, a peptide, a nucleic acid, or a glycan.

8. The conjugate compound of claim 7, wherein the antibody is a monoclonal antibody.

9. The conjugate compound of claim 7 or 8, which is used for MALDI-TOF (Matrix-Assisted Laser Desorption/Ionization Time-Of-Flight) mass spectrometry or matrix-less LDI-TOF (Laser Desorption/Ionization Time-Of-Flight) mass spectrometry.

* * * * *